United States Patent [19]
Ganem et al.

[11] Patent Number: 5,231,185
[45] Date of Patent: Jul. 27, 1993

[54] MONOSACCHARIDE ANALOG-BASED GLYCOSIDASE INHIBITORS

[75] Inventors: Bruce Ganem, Ithaca, N.Y.; Michael K. Tong, Madison, N.J.; George Papandreou, Ithaca, N.Y.

[73] Assignee: Cornell Research Foundation, Inc., Ithaca, N.Y.

[21] Appl. No.: 734,593

[22] Filed: Jul. 23, 1991

Related U.S. Application Data

[63] Continuation-in-part of Ser. No. 453,051, Dec. 13, 1989, abandoned, which is a continuation of Ser. No. 106,486, Oct. 6, 1987, abandoned, which is a continuation-in-part of Ser. No. 799,708, Nov. 19, 1985, abandoned.

[51] Int. Cl.⁵ .................. C07D 211/72; C07D 211/58; C07D 211/40; C07D 211/02
[52] U.S. Cl. .................... 546/296; 546/243; 546/249; 546/257; 546/281; 546/2; 536/18.7
[58] Field of Search ................ 546/257, 296

[56] References Cited

U.S. PATENT DOCUMENTS

5,081,248  1/1992  Zama et al. .................. 546/296

Primary Examiner—Alan L. Rotman
Attorney, Agent, or Firm—Bruce F. Jacobs

[57] ABSTRACT

Broad spectrum glycosidase inhibitors are produced from monosaccharide lactams by conversion to amidines, amidrazones, or amidoximes. The inhibitors have the general formula:

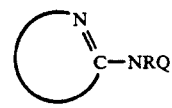

wherein the N and C are joined as part of a monosaccharide azaanalog ring and wherein —NRQ, together with the nitrogen and carbon atoms, form a chemical group selected from amidines, amidrazones, and amidoximes.

4 Claims, 11 Drawing Sheets

MONOSACCHARIDE ANALOG-BASED GLYCOSIDASE INHIBITORS

CROSS-REFERENCE TO RELATED APPLICATIONS

This application is a continuation-in-part of U.S. Ser. No. 07/453,051, filed Dec. 13, 1989, now abandoned which is a continuation of U.S. Ser. No. 07/106,486, filed Oct. 6, 1987, now abandoned, which is a continuation-in-part of U.S. Ser. No. 06/799,708, filed Nov. 19, 1985, now abandoned.

BACKGROUND OF THE INVENTION

This invention relates to amidine, amidrazone and amidoxime derivatives of monosaccharides which have an unexpectedly broad spectrum glycosidase inhibitory effect. The invention further relates to methods of preparing the derivatives, novel intermediates, methods of preparing the intermediates, and the use of the derivatives to inhibit glycosidases, particularly multiple classes thereof.

Glycosidases are enzymes that catalyze the hydrolysis of glycosidic bonds and are essential for the normal growth and development of all organisms. Their vital role is reflected in their wide distribution in nature. They participate in biologically significant reactions such as the breakdown of carbohydrate foodstuffs, the processing of eucaryotic glycoproteins, the catabolism of polysaccharides and glycoconjugates, and the like. Certain glycosidase inhibitors have been found to inhibit human immunodeficiency virus (HIV) syncytium formation and virus replication, thereby indicating their potential use as antiretroviral agents. And some glycosidases are showing promise in treating diabetes or as antiviral and anticancer agents.

Polyhydroxylated piperidines constitute a class of naturally-occurring glycosidase inhibitors. Examples of such monosaccharide analogs which contain a nitrogen atom (an endocyclic nitrogen) in place of the pyranose oxygen include: nojirimycin (A) and 1-deoxynojirimycin (B) (Inouye et al., *Tetrahedron*, 1968, 24, 21252144), 1-deoxymannojirimycin (C) (Fellows et al, *J. Chem. Soc. Chem. Commun.*, 1979, 977-8), and galactostatin (D) (Miyake et al., *Agric. Biol. Chem.*, 1988, 52, 661-6). These alkaloids are quite specific inhibitors of their targeted enzymes. The arrangement of the hydroxyl groups apparently determines individual enzyme specificity of these inhibitors. Compounds A and B are potent glucosidase inhibitors that closely resemble glucose; compound C inhibits mannosidases; and compound D inhibits galactosidases. The inhibitors are believed to function by mimicking the natural substrates. Compound B has been shown to interfere with the infectivity of HIV (Gruters et al., *Nature*, 1987, 330, 74-7).

Since a number of glycosidases are insensitive to the naturally occurring alkaloids, tremendous effort has been devoted to the development of synthetic inhibitors which may inhibit those enzymes. Examples include inhibitors of: jack bean α-mannosidase (E) (Eis et al., *Tetrahedron Lett*, 1985, 26, 5397-8), coffee bean α-galactosidase (F) (Bernotas et al., *Carbohydr. Res.*, 1987, 167, 305-11), α-N-acetylglucoaminidase (G) (Fleet et al., *Chem. Lett.*, 1986, 1051-4), and α-hexosaminidase (H) (Bernotas et al., *Carbohydr. Res.*, 1987, 167, 312-6). In these polyhydroxylated piperidines, the ring oxygen in the sugar has been replaced by a nitrogen to form azasugars. Unfortunately, the analogy of using azasugars as glycosidase inhibitors is not always applicable. For example, while polyhydroxylated pyrrolidines are better inhibitors of yeast α-glucosidase, their relative activities are reversed for a number of mouse gut disaccharides. Therefore, the actual effectiveness of a given compound as a glycosidase inhibitor of a specific enzyme and the effect on specificity by a given structural change of the compound remain unpredictable.

Other potent glycosidase inhibitors contain at the anomeric position an exocyclic nitrogen. (Lai et al., *Biochem. Biophys. Res. Commun.*, 1973, 54, 463-8) For example, glucosylamine inhibits both α- and β-glucosidases.

The present invention is the result of attempting to combine into a single compound several specific features which, among many others, have been found to be present in some glycosidase inhibitors to determine whether the combination compound would prove beneficial. Thus, the compounds of this invention contain both endocyclic and exocyclic nitrogens in an $sp^2$-hybridized functional group and also have a flattened, half-chair conformation. While previous glycosidase inhibitors have generally shown activity only against a single class of glycosidases, i.e. glucosidases, mannosidases, galactosidases, etc., they have not demonstrated broad spectrum activity across multiple classes. The amidine, amidrazone, and amidoxime derivatives of the monosaccharide analogs of the present invention, on the other hand, have been unexpectedly found to exhibit an apparently unique and broad spectrum of glycosidase inhibitory activity which extends across class lines, i.e. independent of the sugar analog from which they are formed.

Previous attempts at preparing amidine derivatives of glucose to form possible glycosidase inhibitors were reported by Bird et al., *Can. J. Chem.*, 1990, 68(2), 317-22. Bird et al. started with glucose and prepared 5-azido-2,3,4,6-tetra-O-benzyl-5-deoxy-D-gluconitrile and 2,3,4,6-tetra-O-benzyl-5-deoxy-5-trifluoroacetamido-D-gluconitrile, but was unable to convert these compounds into a protected 5-amino-5-deoxy-D-gluconitrile and to subsequently cyclize them to an amidine analog of glucose.

Accordingly, it is an object of the present invention to produce glycosidase inhibitors which combine both endocyclic and exocyclic nitrogens into an $sp^2$-hybridized functional group and also have a half-chair conformation.

It is a further object to produce novel amidine, amidrazone, and amidoxime derivatives of monosaccharides.

It is a further object to develop a process for producing glycosidase inhibiting compounds which process could generate amidines, amidrazones or amidoximes of different glycoses by simply changing the configuration of the starting material.

These and still further objects will be apparent from the following detailed description of the invention.

SUMMARY OF THE INVENTION

In accordance with the present invention, novel amidine, amidrazone, and amidoxime derivatives of monosaccharides, i.e. hexoses and pentoses, are synthesized from appropriate thionolactam precursors. The thionolactam precursors are themselves novel compounds and are prepared by the action of Lawesson's reagent on the appropriate lactams in which the hydroxyl groups have been previously protected/blocked.

DESCRIPTION OF THE PREFERRED EMBODIMENTS

Figure 1A:
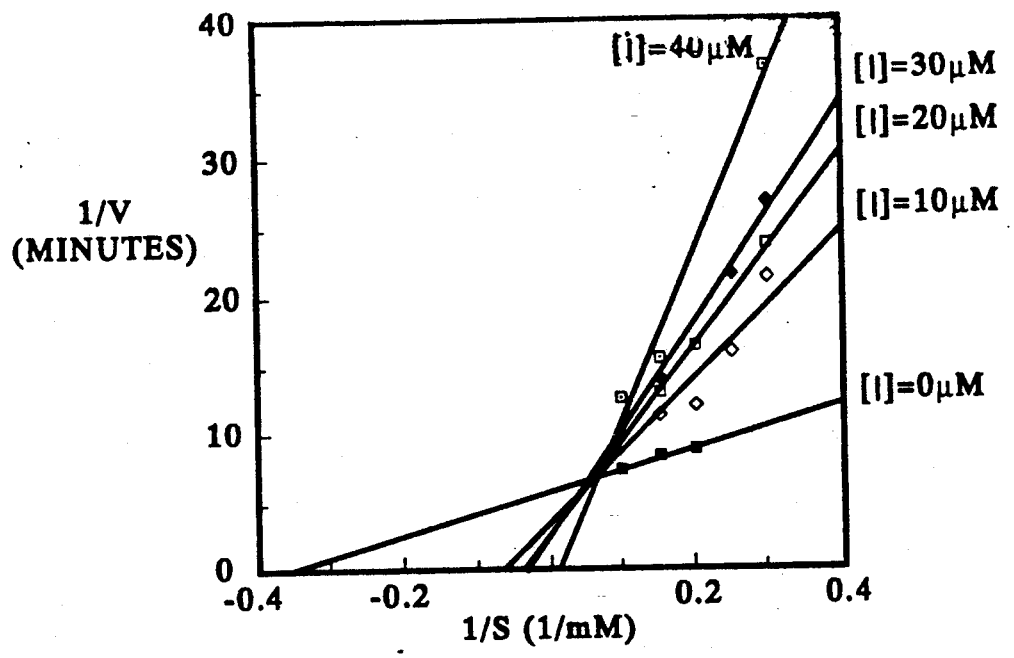
FIGS. 1a and b are the graphs of (a) 1/V vs 1/[S] and (b) L-B slopes vs [I] for the D-glucoamidine of Example 1 against almond β-glucosidase.

The compounds of the present invention combine a halfchair, i.e. flattened anomeric, conformation with both exocyclic and endocyclic nitrogens to form an sp²-hybridized functional group in a monosaccharide which conformation and group produce broad spectrum glycosidase inhibitory activity.

Specific compounds of this invention are derivatives of monosaccharides and have the general formula:

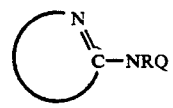

wherein R is selected from hydrogen, alkyl, substituted alkyl, alkaryl, aryl, substituted aryl, aralkyl, and Q is selected from R, —NR₂, and —OH; wherein when Q is R the two R groups may be joined together to form a ring containing at least 2 o carbon atoms; and wherein the —N=C— is part of a monosaccharide azaanalog ring.

Preferably, —NRQ together with the carbon atom to which it is attached and said nitrogen atom form a functional group selected from amidines, amidrazones, and amidoximes.

The amidines have the general formula:

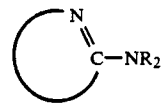

wherein each R is hydrogen or a hydrocarbon group. Suitable hydrocarbon groups are generally selected from alkyl, substituted alkyl, alkaryl, aryl, substituted aryl, aralkyl, or the two R groups are joined together to form a ring containing at least 2 carbon atoms. Preferably each R is hydrogen or alkyl $C_{1-6}$.

The amidrazones have the general formula:

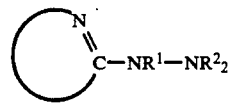

wherein $R^1$ and $R^2$ are each hydrogen or a hydrocarbon group. Suitable hydrocarbon groups are generally selected from alkyl, substituted alkyl, alkaryl, aryl, substituted aryl, aralkyl, or the two $R^2$ groups are joined together to form a ring containing at least 2 carbon atoms.

The amidoximes have the general formula:

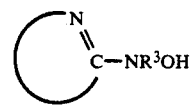

wherein $R^3$ is hydrogen or a hydrocarbon group. Suitable hydrocarbon groups are generally selected from alkyl, substituted alkyl, alkaryl, aryl, substituted aryl, and aralkyl.

Preferred numbers of carbon atoms and substituents for the various hydrocarbon groups in each of the above formulae include: alkyl from 1 to about 18 carbon atoms, substituted alkyl from about 1 to 18 carbon atoms and wherein the substituents do not substantially interfere with the glycosidase inhibitory action of the compounds, alkaryl from 7 to about 18 carbon atoms and which may also be substituted, aryl from 6 to 18 carbon atoms, substituted aryl from 6 to about 18 carbon atoms and wherein the substituents do not substantially interfere with the glycosidase inhibitory action of the compounds, aralkyl from 7 to about 18 carbon atoms. Specific examples of useful substituents include: hydroxypropyl, hydroxybutyl, naphthyl, 2-furyl, imidazolyl, p-methoxyphenyl, p-fluorophenyl, shingosinyl, phenacylmethyl, and the like.

The terminal N of the amidrazones is reactive and thus, either before or after the formation of the amidrazone, it may be reacted with acid halides, anhydrides, esters, isocyanates, isothiocyanates, and the like in a conventional manner. Similarly, the —OH group which is part of the amidoxime functionality of the amidoximes (as opposed to the monosaccharide hydroxyls) is reactive and may be etherified or esterified either before or after formation of the amidoxime.

In the azaanalog derivatives of monosaccharides of this invention, the ——N=C—— portion of the hexose or pentose ring (in which the usual oxygen atom of a monosaccharide has been replaced by a nitrogen atom)

also forms part of the amidine, amidrazone, or amidoxime functional group.

Monosaccharides on which the present analog derivatives are based are hexoses or pentoses which form cyclic structures. Suitable monosaccharides include the glucose and ribose families as well as the stereoisomers, deoxy and substituted derivatives thereof. Specific monosaccharides upon which the azaanalog derivatives of this invention may be based include, for example, (i) aldohexoses: altrose, allose, mannose, glucose, galactose, talose, gulose, idose, fucose, 2-deoxy-2-aminoglucose, 2-deoxy-2-aminogalactose, and the like; (ii) aldopentoses: ribose, arabinose, 2-deoxyribose, 2-deoxyarabinose, and the like. Preferred such monosaccharides are mannose, glucose, galactose, fucose, 2-deoxy-2-aminoglucose, 2-deoxy-2-aminogalactose, ribose, arabinose, 2-deoxyribose, and 2-deoxyarabinose. The currently most preferred monosaccharides are glucose, mannose, and galactose due to the ready availability of lactams thereof which are starting materials for the preparative part of this invention.

The preparation of the compounds of the invention will be described herein commencing from the lactams of a monosaccharide. Lactams are organic compounds which contain an —NH—CO— group within a ring. They are generally formed by the elimination of water from neighboring carboxyl and amino groups. The monosaccharide lactams of the present invention are therefore cyclic amides having the general structure:

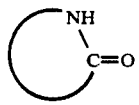

The reactions used herein to convert a lactam to the corresponding amidines, amidrazones, and amidoximes of the invention are independent of both the stereochemistry and the size of the balance of the monosaccharide ring. Thus the present invention is applicable to any monosaccharide. Numerous references to the preparation of lactams of monosaccharides have been reported in the recent chemical literature. The references include: Inouye et al., Tetrahedron, 1968, 24(5), 2125–44; Hanessian, J. Org. Chem., 1969, 34(3), 675–81; Ito et al., JP 46-024,382, 1971; Tsuruoka et al., Meiji Seika Kenkyu Nempo, 1973, No. 13, 80–4; Niwa et al., U.S. Pat. No. 3,956,337; Tsuruoka et al., JP 50-129,572; Niwa et al., J. Antibiot., 1984, 37(12), 1579–86; Ehata et al., JP 61-280,472; Miyake et al., Agric. Biol. Chem., 1988, 52(3), 661–6; Shing, J. Chem. Soc. Chem. Commun., 1988, 18, 1221; Fleet et al., Tetrahedron, 1989, 45(1) 319–26;Tsuruoka et al., JP 63-258,421 and JP 63-216,867; Fleet et al., Tetrahedron Lett., 1990, 31(3), 409–12.

A particularly suitable procedure for preparing D-gluconolactam, i.e. the lactam of D-glucose, by the oxidation of nojirimycin is described in Example 1 below. This procedure represents an improved oxidation procedure over previous procedures in that the yield obtained is significantly higher than the published yield, i.e. about 50% vs. about 30%.

Other monosaccharide lactams may be prepared in accordance with one or more of the preparative procedures cited above.

The hydroxyl groups of the monosaccharide lactams are then protected from reaction with Lawesson's reagent which is subsequently used to form thionolactams which are then reacted with NH-containing compounds to yield the desired functional compounds. Suitable blocking/protecting groups are those that, for a particular lactam, do not participate in neighboring group interactions which result in the formation of undesired compounds. Preferably, the groups will also be removable under relatively mild conditions. Examples of such suitable groups include trimethylsilyl, acetyl, t-butyldimethylsilyl, trityl, methoxymethyl, benzyl, and benzoyl.

The protecting groups may be incorporated onto the lactams by any conventional suitable manner. For example, trimethylsilyl groups may be produced by suspending the lactam in a non-solvent, such as dry pyridine; adding a mixture of chlorotrimethylsilane and hexamethyldisilazane; stirring at room temperature; and then recovering the resulting persilylated lactam. Acetyl groups may be provided by peracetylation with $Ac_2O$, NaOAc, at room temperature for extended periods.

The protected hydroxyl group-containing lactam is then converted to the corresponding thionolactam by reaction with Lawesson's reagent (p-methoxyphenylthionophosphine sulfide dimer) in a conventional manner, i the protected lactam in a solvent such as benzene under an inert gas such as argon at room temperature and then heating to reflux. Lawesson's reagent and its use are described in Scheibye et al., Bull. Soc. Chem. Belg., 1978, 87, 229–38. The reaction with Lawesson's reagent converts the C=O of the lactam to a C=S of the thionolactam without disturbing the protecting groups.

The protecting groups are then removed in a conventional manner such as by acidic hydrolysis. Any sufficiently strong acid which does not effect the balance of the compounds may be used. Suitable such acids include hydrochloric acid, sulfuric acid, perchloric acid, fluoroboric acid, p-toluenesulfonic acid, and the like. Other methods of removing protecting groups include hydrogenolysis, alcoholysis, and fluoride treatment. Alternatively, when the final products are sufficiently stable the protecting groups may be allowed to remain on the thionolactam during reaction with the NH-compound and then removed as discussed.

The thionolactams of the monosaccharides produced are believed novel compounds themselves. They are useful intermediates in the preparation of the glycosidase inhibitors. Specifically, depending upon the particular NH-containing compound with which they are reacted, they may yield amidine, amidrazone, and amidoxime derivatives.

Thus, the glycosidase inhibitor compounds of the present invention are ultimately synthesized by reaction of monosaccharide thionolactam precursors of the general formula:

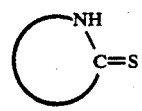

with an NH-containing compound, preferably in solution. Suitable solvents include water, alcohols, acetonitrile, and the like. Preferably the solvent is methanol, ethanol,isopropyl alcohol or acetonitrile. Suitable temperatures will range from about 0° C. to reflux.

The amidine derivatives are readily prepared by reacting the thionolactam with ammonia or the appropriate mono- or disubstituted amine. Suitable such amines or ammonia are those of the formula $NHR_2$ wherein each R is independently selected from hydrogen, alkyl, substituted alkyl, alkaryl, aryl, substituted aryl, aralkyl, or the two R groups are joined together to form a ring contain at least 2 and generally less than about 8 carbon atoms.

The amidrazone derivatives are prepared in like manner to the amidines but with the thionolactam being reacted with hydrazine or a hydrazine derivative, generally of the formula $NHR^1$-$NR^2_2$ wherein $R^1$ and each $R^2$ are individually selected from hydrogen, alkyl, substituted alkyl, alkaryl, aryl, substituted aryl, aralkyl, or the two $R^2$ groups are joined together to form a ring contain at least 2 carbon atoms and generally less than about 8 carbon atoms. Either before or after formation of the amidrazone, the terminal N of the hydrazine compound may be reacted with an acid halide, anhydride, ester, isocyanate, isothiocyanate or the like.

The amidoxime derivatives are also prepared in like manner to the amidines and amidrazones but with the thionolactam being reacted with a hydroxyamine of the general formula $NHR^3OH$ wherein $R^3$ is selected from hydrogen, alkyl, substituted alkyl, alkaryl, aryl, substituted aryl, and aralkyl. Either before or after formation of the amidoxime, the OH-group may be esterified or etherified by reaction with an acid halide, anhydride, ester, isocyanate, isothiocyanate or the like.

While the degree of glycosidase inhibitory activity on a particular glycosidase enzyme or series of glycosidase enzymes is likely to at least partially depend upon the specific R groups which are provided on specific compounds, the principles of this invention have not been found dependent thereon. Preferred numbers of carbon atoms and substituents for the various groups in each of the above formulae include: alkyl from 1 to about 10 carbon atoms, substituted alkyl from about 1 to 10 carbon atoms and wherein the substituents do not substantially interfere with the glycosidase inhibitory action of the compounds, alkaryl from 7 to about 18 carbon atoms and which may also be substituted, aryl from 6 to 18 carbon atoms, substituted aryl from 6 to about 18 carbon atoms and wherein the substituents do not substantially interfere with the glycosidase inhibitory action of the compounds, aralkyl from 7 to about 18 carbon atoms. Examples of specific substituents include: halogens, alkyl, aryl, alkoxy, fluoro, cyano, carboalkoxy, reto, thio, nitro, and the like.

The glycosidase inhibitors of this invention are generally useful with a broad spectrum of glycosidase enzyme classes as opposed to a single class. While the general inhibitory strength of a particular compound will vary depending upon its particular structure and the enzyme, the compounds of this invention have exhibited potent inhibitory effects against glucosidases, mannosidases, and galactosidases. Other classes of glycosidase enzymes for which the inhibitors are likely to be useful include one or more of: L-fucosidases, sialidases, glucosaminidases, chitinases, lysozyme, cellulases, and the like. Specific glycosidase enzymes which have been inhibited by one or more of the claimed compounds include yeast α-glucosidase, *aspergillus niger* amyloglucosidase, almond β-glucosidase, jackbean α-mannosidase, green coffee bean α-galactosidase, and bovine liver β-galactosidase.

While the D-glucoamidines have been found to be potent inhibitors against gluco, manno and galactosidases, they have also proved to be unexpectedly labile, undergoing rapid hydrolysis above pH 7. The amidrazone and amidoxime derivatives are much more stable and they were unexpectedly found to be generally even more potent inhibitors, further emphasizing the importance of binding interactions with the anomeric region of the glycosyl cation. The amidoximes represent the first near-neutral monosaccharide analogs possessing the half-chair conformation of the glycosyl intermediates.

GENERAL EXPERIMENTAL INFORMATION

Proton NMR spectra were taken on a Bruker WM-300 spectrometer. All chemical shifts were reported on the δ scale in parts per million downfield from $Me_4Si$. Spectra taken in $CDCl_3$ were referenced to either $Me_4Si$ (0.00 for compounds with aromatic protons) or residual $CHCl_3$ (7.24, for compounds without aromatic protons). Spectra taken in $D_2O$ were referenced to HOD (4.67), and those in $CD_3OD$ were referenced to $CHD_2OD$ (3.30). Carbon-13 NMR spectra were taken on a Varian XL-400 (100 MHz), Bruker WM-300 (75 MHz) spectrometer and referenced to p-dioxane (66.5 ppm) or $CH_3OH$ (49.0 ppm). Infrared spectra were taken on a Mattson Galaxy Model infrared spectometer. Ultraviolet absorption spectra were measured on a Hewlett-Packard HP 8451 A Diode Array Spectrometer. Mass spectra were obtained from a Finnigan 3300 mass spectrometer. Chemical ionization spectra were obtained using isobutane as reagent gas; electron impact spectra were run at 70 e V ionizing voltage. Fast atom bombardment spectra were obtained in glycerol matrix on a Kratos MS-890 Spectrometer. Optical rotations were measured on a Perkin Elmer 24 polarimeter. Sample concentrations were expressed in grams of sample per 100 cc of solvent. High performance liquid chromatography was performed with an Eldex 9600 system using a μ-Porasil column (internal diameter 7.8 mm).

Anhydrous methanol was prepared by distillation from $Mg(OCH_3)_2$. Benzene, pyridine, chlorotrimethylsilane and hexamethyldisilane were dried and distilled from $CaH_2$. All enzymes were obtained from Sigma and used as it.

In the following non-limiting examples, all parts and percents are by weight unless otherwise specified. Also, the compounds produced were generally isolated as their quaternary acetate salts, though other salts may be substituted in a conventional manner.

EXAMPLE 1

Preparation of Glucoamidine

Oxidation of (+)-Nojirimycin to (3R,4S,5R,6R)-6-Hydroxymethyl-3,4,5-trihydroxy-2-piperidone [D-(+)-Gluconolactam To a stirred suspension of nojirimycin bisulfite addition product (1.02 g, 4.22 mmol; Baeyer AG) in distilled water (25 mL) was added activated Dowex 1×2-200 resin (HO-form, 10 g, Aldrich) to make the pH 8-10. After stirring 30 min at room temperature, the resin was filtered, rinsed with distilled water (160 mL) and the combined filtrates lyophilized to afford a crude sample of (+)-nojirimycin (0.89 g, $R_f$ 0.58 in 4:1 ethanol:$H_2O$) which was dissolved in distilled water (15 mL) and used immediately in the next step.

The magnetically stirred aqueous nojirimycin solution was treated with alternating portions of 0.1M I$_2$-0.5M KI solution (83 mL; 2 mL aliquots) and 0.1M NaOH (100 mL, 2.5 mL aliquots) at room temperature slowly over a period of 90 min. After 24 hours, the brown solution was decolorized by addition of aqueous NaHSO$_3$ (1M, 4 mL), then Amberlite IR-120 (H+) resin was added (0.5 g, Aldrich) to bring the pH to 1. After stirring 4 hr at room temperature, the resin was filtered and rinsed with water (50 mL). The combined filtrates were then neutralized with Dowex MWA-1 (Serva Corp.), the resin filtered and washed, and the combined filtrates (ca. 400 mL) concentrated at the rotary evaporator to afford the crude lactam as a white solid. A small portion was chromatographed and recrystallized from ethanol:water to afford pure lactam whose mp (203° C.) and chiroptical properties were identical with published values.

Silylation of Lactam

Crude (5–6 g) was suspended in dry pyridine (20 mL), then (trimethylsilyl)$_2$NH(5 mL) and trimethylsilylchloride (3 mL) was added and the dark brown reaction mixture stirred at room temperature for 90 minutes. Concentration in vacuo afforded a brownish foam (1.6 g) which was flash chromatographed on SiO$_2$ (40 mm×4.5 inch column; 7:1 hexanes:ethyl acetate; 8 mL fractions collected) to furnish the persilylated gluconolactam (1.14 g, 2.46 mmol, 50%): Rf 0.27 (1:7 hexanes:ethyl acetate); [α]$_D$+71° (c=0.54, CHCl$_3$); $^1$H-NMR δ (CDCl$_3$) 5.88 (br. s, 1H), 3.87 (d, 1H, J=8.6 Hz), 3.78 dd, 1 H, J=8.3, 1.8 Hz), 3.69 (dd, 1 H, J=8.7, 8.6 Hz), 3.43 (dd, 1 H, J=8.4, 8.4 Hz), 3.35–3,25 (m, 2H), 0.18 (s, 9 H), 0.14 (s, 18 H), 0.09 (s, 9 H); $^{13}$C-NMR (CDCl$_3$) 170.9, 76.2, 74.0, 71.4, 63.7, 57.0, 0.91, 0.73, −0.70; IR (film) 3210, 3110, 2980, 2905, 1690, 1320, 1250, 1130, 950, 840 cm$^{-1}$; CIMS (methane) m/e 478 (M+2, 65%) 466 (M+1, 50%) 450 (M+-CH$_3$, 100%).

Formation of D-Glucothionolactam (3R,4S,5R,6R)-6-Hydroxymethyl-3,4,5-trihydroxy-2-thionopiperidone To a solution of the persilylated lactam of above (0.284 g, 0.61 mmol) in benzene (15 mL) under argon at room temperature was added Lawesson's reagent (p-methoxyphenylthionophosphine sulfide dimer, 0.148 g, 0.6 equiv) and the suspension was warmed. At 65° C. the reaction became homogeneous and was brought to reflux for 30 min. After concentrating in vacuo, the residue was dissolved in CH$_3$OH (16 mL), acidified (1:9 conc. HCl:CH3OH, 10 drops) and stirred for 35 minutes at room temperature. Concentration afforded a white solid (0.25 g) which was flash chromatographed over SiO$_2$ (20 mm×6 inch column; 7:3:1 CH$_2$Cl$_2$ CH$_3$OH:NH$_4$OH, 3 mL fractions) to afford slightly impure glucothionolactam (0.105 g) which was further purified as follows.

The thionolactam (0.105 g) was dissolved in distilled water (10 mL) and stirred with Norit A (1.0 g) for 30 minutes. The Norit was filtered, rinsed with water (10 mL, discarded), then eluted with 1:1 ethanol:H$_2$O and the eluant concentrated in vacuo to give analytically pure thionolactam (74 mg, 0.38 mmol, 63%): R$_f$ 0.33 (7:3:1 CH$_2$Cl$_2$:CH$_3$OH:NH$_4$OH) mp 126°–128° C.; [α]$_D$+31° (c=0.72, CH$_3$OH) $^1$H-NMR δ (D$_2$O) 3.90 (d, 1 H, J=9.5 Hz) 3.78 (dd, 1 H, J=12.3, 2.4 Hz), 3.74 (dd, 1 H, J=9.8, 8.7 Hz), 3.67 (dd, 1 H, J=12.4, 4.1 HZ), 3.60 (dd, 1 H, J=9.7 Hz), 3.33 (m, 1 H); $^{13}$C-NMR (D$_2$O, acetone ref.) 214.8, 74.2, 72.6, 67.4, 61.6, 59.7; IR (KBr) 3360, 2940, 2900, 1660, 1560, 1450, 1292, 1075, 1030 cm$^{-1}$.

High Resolution FAB-MS: Calculated for C$_6$H$_{11}$NO$_4$S: 193.0409, Found: 193.0403.

Analysis for C$_6$H$_{11}$NO$_4$S: Calculated: C, 37.29; H, 5.74; N, 7.25; S, 16.56, Found C, 36.17; H, 5.87; N, 7.22; S, 13.94 .

Preparation of D-Glucoamidine

Saturated anhydrous NH$_3$ in methanol (1.5 mL) was added dropwise to a stirred solution of the thionolactam (14 mg, 0.072 mmol) in anhydrous CH$_3$OH (1 mL) at room temperature under argon. Thin layer chromatographic monitoring indicated that the thionolactam disappeared in 11 hours and two new spots were visible (baseline and R$_f$0.08 in 7:3:1 CH$_2$Cl$_2$:CH$_3$OH:NH$_4$OH). The solution was concentrated in vacuo, redissolved in fresh CH$_3$OH (2.5 mL) and acidified to pH 3.5 with anhydrous HCl—CH$_3$OH (0.5 mL, prepared from 0.3 mL AcCl in 8 mL CH$_3$OH). Concentration in vacuo afforded a brown oil which was purified by SiO$_2$ flash chromatography (8 mm×2.5 inch column; 20:4:1 CH$_3$CN:H$_2$O:HOAc, 2 mL fractions) to afford the amidine HOAc (11.6 mg, 68%): R$_f$ 0.14 (20:4:1 CH$_3$CN:H$_2$O:HOAc); [α]$_D$+27° (c=0.17, CH$_3$OH); $^1$H-NMR δ (D$_2$O) 4.24 (d, 1 H, J=9.6 Hz), 3.77–3.56 (m, 4 H), 3.34 (m, 1 H) 1.94–1.76 (s, e H), $^{13}$C-NMR (d20, dioxane ref), 179.0, 167.5, 72.0, 68.2, 67.3, 60.1, 59.3, 21.9; IR (KBr) 3390, 3240, 2930, 1685, 1575, 1555, 1415, 1075 cm$^{-1}$.

High Resolution FAB-MS: Calc. for C$_6$H$_{13}$N$_2$O$_4$: 177.0875; Found: 177.0875.

EXAMPLE 2

Preparation of D-Gluco-N,N-Dimethylamidine

Anhydrous dimethylamine was bubbled into dry CH$_3$OH (5 mL) under argon at 0° C. until the volume of the solution doubled. Four milliliters of this solution was transferred by Teflon cannula to the thionolactam of Example 1 (11 mg, 0.057 mmol) and the resulting solution was stirred 10 minutes at 0° C. before warming to room temperature. Thin layer chromatographic monitoring indicated that the thionolactam disappeared in 8 hours and one new spot was visible (R$_f$0.17 in 20:4:1 CH$_3$CN:H$_2$O:HOAc). The solution was concentrated in vacuo. redissolved in fresh CH$_3$OH (3 mL) and acidified under argon to pH 3.0 with anhydrous HCl—CH$_3$OH (0.4 mL, prepared from 0.3 mL AcCl in 8 mL CH$_3$OH). After concentrating in vacuo the residue was purified by SiO$_2$ flash chromatography (8 mm×2.5 inch column; 20:4:1 CH$_3$CN: H$_2$O:HOAc, 2 mL fractions) to afford the amidine.HOAc (10.6 mg, 71%): R$_f$ 0.21 (20:4:1 CH$_3$CN:H$_2$O:HOAc); [α]$_D$+15° (c=0.57, CH$_3$OH); $^1$H-NMR δ (D$_2$O) 4.46 (d, 1 H, J=7.0 Hz), 3.86 (dd, 1 H, J=11.6, 9.0 Hz), 3.77 (dd, 1 H, J=9.0, 7.0 Hz), 3.71 (dd, 1 H, J=12,2, 3.8 Hz) 3.60 (dd, 1 H, J=11.6, 9.0 Hz), 3.45 (m, 1 H), 3.21 (s, 3H), 3.04 (s, 3H); $^{13}$C-NMR (D$_2$O, dioxane ref) 179.7, 163.2, 74.5, 68.9, 65.9, 58.9, 58.6, 41.7, 39.4, 22.2; IR (KBr) 3320, 2925, 1660, 1565, 1420, 1060 cm$^{-1}$.

High Resolution FAB-MS: Calculated for C$_8$H$_{16}$N$_2$O$_4$: 204.1111; Found: 204.1110.

EXAMPLE 3

Preparation of D-Mannoamidines

L-gluconolactone was converted to D-mannolactam by the procedure of Fleet (1989). As described in detail in Example 9 below, the hydroxyl groups of the lactam were blocked with trimethylsilyl groups, and the lactam converted to the thionolactam. Then the amidine was formed by reaction of the thionolactam with ammonia in methanol at room temperature and the blocking groups removed, all as done in Example 1 for D-gluconolactam.

A portion of the D-mannothionolactam is also reacted with diethylamine to produce the corresponding D-manno-N,N-diethylamidine.

EXAMPLE 4

Preparation of D-Galactoamidines

The procedure of Example 1 is repeated to produce two D-galactoamidines by reacting D-galactothionolactam (produced from galactostatin) in one case with ammonia and in the other with benzylamine. The resulting compounds are D-galactoamidine and D-galacto-N-benzylamidine.

EXAMPLE 5

Preparation of L-Idoamidine

The procedure of Example 1 is repeated to produce two L-idoamidines by reacting L-idothionolactam (produced by the procedure of Ito et al., JP 46-024382) in one case with ammonia and in the other with diphenylamine. The resulting compounds are L-idoamidine and L-ido-N,N-diphenylamidine.

EXAMPLE 6

Preparation of D-Glucoepiminoamidine

The procedure of Example 1 is repeated to produce D-glucoepiminoamidine by reacting D-glucothionolactam with ethyleneimine in ethanol. The resulting compound is D-glucoepiminoamidine which has the exocyclic nitrogen atom in a three membered ring with two carbon atoms.

EXAMPLE 7

Preparation of Riboamidines

The basic procedure of Example 1 is repeated to produce two D-riboamidines by reacting D-ribothionolactam (produced by the procedure of Hanessian, *J. Org. Chem.*, 1969, 34 (3), 675–81) in one case with ammonia and in the other with dimethylamine. The resulting compounds are D-riboamidine and D-ribo-N,N-dimethylamidine.

EXAMPLE 8

Preparation of D-Glucoamidrazone

Anhydrous $NH_2NH_2$ (70 μL, 2.208 mmol, distilled from NaOH) was added dropwise to a stirred solution of D-gluconothionolactam (20.5 mg, 0.106 mmol) in anhydrous $CH_3OH$ (3 mL) in an ice-$H_2O$ bath under Ar. TLC monitoring ($CH_3CN:OAc:H_2O$ 20:1:4) indicated that the thionolactam disappeared after 90 min. The solution was concentrated in vacuo and the residue (24 mg) was purified by $SiO_2$ chromatography (3.5 in×12 mm column; 25:3:1 $CH_3CN:H_2O:HOAc$, 2 mL fractions) to afford D-glucoamidrazone HOAc (19.3 mg, 73%): $R_f = 0.33$ ($CH_3CN:AcOH:H_2O$ 10:1:4) $[\alpha]_D + 15.6°$ (c=0.45, MeOH); $^1$H-NMR δ ($D_2O$) 4.27 (m, 1 H, J=2.3, 6.9 Hz), 3.81 (dd, 1 H, J=2.8, 12.2 Hz), 3.72–3.67 (m, 3 H), 3.41 (m, 1 H), 1.78 (s,3 H); $^{13}$C-NMR ($D_2I$, dioxane ref.), 179.1, 164.4, 72.4, 67.7, 60.2, 59.1, 22.2, IR (KBr), 3310, 2920, 1700, 1665, 1560, 1410, 1110, 1070, 1020 cm$^{-1}$.

High Resolution FAB-MS: Calc. for $C_6H_{14}O_4N_3$: 192.0984; Found: 192.0989.

EXAMPLE 9

Preparation of D-Mannoamidrazone

Preparation of D-Mannonothionolactam

D-Mannolactam (0.203 c, 1.14 mmol) was dissolved in dry pyridine (15 mL), then $(TMS)_2NH$ (5 mL) and TMSCl (2.5 mL) were added dropwise. The resulting suspension was stirred at room temperature under Ar for 90 min. Concentration in vacuo afforded a white residue (613 mg) which was triturated with hexanes (60 mL in 3 mL fractions). The combined triturants were concentrated using a rotary evaporator to yield the corresponding persilylated lactam (0.533 g, 93%): $R_f = 0.20$ (hexane:EtOAc 7:1); $^1$H-NMR δ ($CDCl_3$) 6.11 (s, 1 H, broad) 4.3 (d, 1 H, J=2.7 Hz), 3.76 (dd, 1 H, J=4.5, 2.7 Hz), 3.7 (m, 1 H), 3.56–3.51 (m, 2 H), 3.26 (m, 1 H), 0.12–0.0 (m, 36 H); IR ($CHCl_3$), 3390, 2970, 1675, 1460, 1310, 1250, 1100 cm$^{-1}$; $^{13}$C-NMR δ ($CDCl_3$) 170.5, 74.9, 69.3, 68.8, 64.1, 60.6, 0.10, 0.05, −0.21, −0.87. To a solution of the persilylated mannolactam (176 mg, 0.378 mmol) in benzene (12 mL) under Ar was added Lawesson's reagent (136 mg, 0.337 mmol) and the suspension was heated to reflux for 1 h. After concentrating the homogeneous reaction mixture in vacuo, the residue was suspended in $CH_3OH$ (10 mL), acidified [8 drops from a solution of $CH_3OH$ (10 mL) and AcCl (0.3 mL)] whereupon it became homogeneous after 90 minutes at room temperature. Concentration afforded a white solid (230 mg) which was triturated with $CHCl_3$ (30 mL in 2 mL portions). The residue (81.2 mg) was purified by $SiO_2$ chromatography on a 5 inch×15 mm column eluting with $CH_3CN:H_2O:AcOH$ 200:4:1 (3 mL fractions) to afford D-mannothionolactam (38 mg, 53%): $R_f = 0.30$ ($CH_2Cl_2$ $CH_3OH:NH_4OH$ 7:3:1); $[\alpha]_D + 53.3°$ (c=0.69, MeOH); $-^1$H-NMR δ ($D_2O$) 4.29 (d, 1 H, J=3.7 Hz), 3.94 (dd, 1 H, J=3.8, 5.4 Hz), 3.8 (dd, 1 H, J=12.0, 3.6 Hz), 3.77 (dd, 1 H, J=5.3, 7.1 Hz), 3.66 (dd, 1 H, J=5.6, 12.0 Hz), 3.32 (m, 1 H); $^{13}$C-NMR δ ($D_2O$, dioxane ref.) 202.8, 72.7, 72.0, 67.7, 60.9, 60.5; IR (KBr) 3390, 2910, 1620, 1540, 1390, 1120, 1060; CIMS 194 (M+1, 100%); EI-MS 193 (M+, 100%), 157 (96%), 140 (29%), 139 (26%), 111 (54%), 102 (32%).

Preparation of D-Mannoamidrazone

Anhydrous $NH_2NH_2$ (60 μL, 1.89 mmol, distilled from NaOH) was added dropwise to a stirred solution of the D-manno-thionolactam above (14 mg, 0.072 mmol) in anhydrous $CH_3OH$ (3 mL) in an ice-$H_2O$ bath under Ar. TLC monitoring ($CH_3CN:AcOH:H_2O$ 20:1:4) indicated that the starting material disappeared in 90 minutes. The solution was concentrated in vacuo and the residue (16 mg) was purified by $SiO_2$ chromatography (17 mm×6 cm column; 25:3:1 $CH_3CN:H_2O:AcOH$·2 mL fraction) to afford D-mannoamidrazone HOAc (14 mg, 75%): $R_f=0.35$ ($CH_3CN:H_2O:AcOH$ 10:4:1); $[\alpha]_D + 10.9°$ (c=0.46, $CH_3OH$); $^1$H-NMR δ ($D_2O$) 4.64 (d, 1 H, J=3.4 Hz), 3.97 (dd, 1 H, J=3.6, 4.8 Hz), 3.89 (dd, 1 H, J=4.9 Hz), 3.78 (dd, 1 H, J=4.5, 11.8 Hz) 3.67 (dd, 1 H, J=5.9, 11.8 Hz), 3.37 (m, 1 H), 1.84 (s, 3 H); $^{13}$C-NMR $\delta$ (D$_2$O, dioxane ref.) 179.1, 164.1, 70.8, 67.5, 64.7, 61.1, 58.2, 22.1; IR (KBr) 3290, 2930, 1705, 1575, 1410, 1350, 1120, 1065, 101 cm$^{-1}$.

High Resolution FAB-MS: Calc. for C$_6$H$_{14}$O$_4$N$_3$: 192.0984; Found: 192.0980.

EXAMPLE 10

Preparation of D-Galacto-N,N-Dimethylamidrazone

The procedure of Example 4 is repeated to produce D-galactothionolactam which is reacted with 1,1-dimethylhydrazine as in Example 8 to produce D-galacto-N,N-dimethylamidrazone.

EXAMPLE 11

Preparation of Riboamidrazone

The procedure of Example 8 is repeated to produce D-ribothionolactam which is reacted with hydrazine as in Example 8 to produce D-riboamidrazone.

EXAMPLE 12

Preparation of D-Glucoamidrazone-N-Phenylurea

The procedure of Example 8 is repeated except that the hydrazine is replaced by an equivalent amount of 4-phenylsemicarbazide (NH$_2$-NH-CONHPh and the solvent is acetonitrile. Reaction readily occurs to produce the D-glucoamidrazone-N-phenylurea.

EXAMPLE 13

Preparation of D-Glucoamidoxime

Preparation of D-Glucoamidoxime

Anhydrous hydroxylamine (200 μL of a 1.25M CH$_3$OH solution) was added under Ar to a stirred solution of D-gluconothiolactam (10 mg, 0.052 mmol) in CH$_3$OH (2.5 mL). After 14 hours at room temperature, the lactam was completely consumed and a new spot had appeared at Rf 0.14 (CH$_2$Cl$_2$ CH$_3$OH:NH$_2$OH 7:3:1). The solution was concentrated in vacuo and the residue (17 mg) was purified by SiO$_2$ chromatography (3"×16 mm column; CH$_3$CN:H$_2$O:HOAc 30:3:1, 2 mL fractions) to afford D-glucoamidoxime HOAc (10 mg, 75%): Rf 0.41 (CH$_3$CN:H$_2$OHOAc 10:4:1); [α]$_D$+62° (c=0.39, CH$_3$OH); $^1$H-NMR $\delta$ (D$_2$O) 4.49 (d, 1 H, J=10.1 Hz), 4.18 (dd, 1 H, J=2.2 Hz), 3.86 (dd, 1 H, J=2.3, 10.1 Hz), 3.69 (m, 3 H), 1.83 (s, 3 H); $^{13}$C-NMR $\delta$ (D$_2$O, CH$_3$OH ref.) 179.1, 156.4, 74.3, 68.4, 60.9, 57.8, 22.0,; IR (KBr) 3400, 2920, 1660, 1590, 1570, 1420, 1335, 1110, 1020 cm$^{-1}$.

High Resolution FAB-MS: Calc. for C$_6$H$_{13}$O$_5$N$_2$: 193.0824; Found: 193.0821.

EXAMPLE 14

Preparation of D-Gluco-N-Methylamidoxime

The procedure of Example 13 is repeated except that the hydroxylamine is replaced by an equivalent amount of N-methylhydroxylamine to produce the D-gluco-N-methylamidoxime.

EXAMPLE 15

Preparation of D-Mannoamidoxime

Anhydrous hydroxylamine (prepared as above, 280 μL) was added under Ar to a stirred solution of mannonothiolactam IX (12.2 mg, 0.063 mmol) in CH$_3$OH (2.5 mL). After 24 hours at room temperature, the D-mannolactam was completely consumed and a new spot had appeared at Rf 0.10 (CH$_2$Cl$_2$:CH$_3$OH:NH$_2$OH 7:3:1). The solution was concentrated in vacuo and the residue (16 mg) was purified by SiO$_2$ chromatography (2"×16 mm column: CH$_3$CN:H$_2$O:HOAc 30:3:1, 1.5 mL fractions) to afford D-mannoamidoxime HOAc (11.6 mg, 73%): Rf 0.60 (CH$_3$CN:H$_2$O:HOAc 10:4:1); [α]$_D$−1.0.(c=0.40, CH$_3$OH); $^1$H-NMR $\delta$ (D$_2$O) 4.64 (d, 1 H, J=2.2 Hz), 3.38 (m, 1 H), 1.95 (s, 3 H); 13C-NMR $\delta$ (D$_2$O, CH$_3$OH ref.) 178.8, 156.0, 71.6, 66.5, 66.4, 61.7, 58.1, 21.8,; IR (KBr) 3390, 2930, 1660, 1560, 1545, 1420, 1340, 1100, 1055, 1010 cm$^{-1}$.

High Resolution FAB-MS: Calc. for C$_6$H$_{13}$O$_5$N$_2$: 193.0824; Found: 193.0825.

EXAMPLE 16

Preparation of L-Idoamidoxime

The procedure of Example 5 is repeated to produce L-idothionolactam which is reacted with hydroxylamine as in Example 12 to produce L-idoamidoxime.

EXAMPLE 17

Preparation of D-Glucoamidoxime-N-Phenylurethane

The D-glucoamidoxime of claim 13 is reacted with phenyl isocyanate in acetonitrile at a temperature ranging from 0° C. to room temperature to substantially quantitatively produce the D-glucoamidoxime-N-phenylurethane.

GENERAL BIOLOGICAL PROCEDURES

A. Preparation of Solutions for Enzyme Assays

Phosphate Citrate Buffers—Phosphate-citrate buffers at constant ionic strength (0.5M) were prepared according to a published procedure.(2)

HOAc/NaOAc Buffer—To an aqueous solution of acetic acid (0.4M, 100 mL) was added aqueous sodium acetate (0.4M, 100 mL). The resulting solution was adjusted to pH 5.0 by addition of aqueous sodium hydroxide (6.0M).

NaCl/NaOAc Buffer—A mixture of aqueous NaCl solution (0.1M, 2.0 mL) and HOAc/NaOAc buffer (0.75 mL) was diluted with deionized water (17.25 mL) to yield NaCl/NaOAc buffer (pH 5.0).

Glycine Buffer—Glycine (22.47 g, 0.299 mol) was dissolved in deionized water (705 mL, final concentration: 0.42M). The resulting solution was adjusted to pH 10.4 by aqueous NaOH (6.0M).

pH for Enzyme Assays—Yeast α-glucosidase and green coffee bean α-galactosidase were assayed at pH 6.6. Almond β-glucosidase and jackbean α-mannosidase were assayed at pH 5.0. Bovine liver β-galactosidase was assayed at pH 7.0.

Working Enzyme Solutions—Typical enzyme concentrations in the assay buffer for inhibitor screening were as follows: yeast α-glucosidase, 10 μL of enzyme suspension in 2.00 mL pH 6.6 phosphate-citrate buffer; almond β-glucosidase, 25 μL of enzyme solution (0.4 mg solid enzyme in 70 μL pH 5.0 NaCl/NaOAc buffer) in 5.00 mL pH 5.0 NaCl/NaOAc buffer; jackbean α-mannosidase, 5–8 μL of enzyme suspension in 2.00 mL NaCl/NaOAc buffer; green coffee bean α galactosidase, 15 μL of enzyme suspension in 1.2 mL NaCl/NaOAc buffer; bovine liver β-galactosidase, 1.7 mg solid enzyme in 850 μL NaCl/NaOAc buffer.

B. General Assay Procedure

An acceptable concentration of enzyme, upon hydrolysis of the corresponding glycoside, should give an absorbance reading between 0.4 and 2.0 at 400 nm. A control assay was first performed to determine whether the enzyme concentration was acceptable. The assays involved addition of working enzyme solution (0.09 mL) and deionized water (0.18 mL) to buffer at the appropriate pH (0.09 mL, phosphate-citrate). The resulting solution was incubated at 37° C. for 5 minutes. Aliquots (0.1 mL) of this preincubation mixture was then added to three separate test tubes. Substrate (the corresponding p-nitrophenyl-D-glycoside, 0.1 mL, 10 mM in appropriate buffer), which had also been incubated at 37° C., was then added to each tube at thirty-second intervals. The hydrolyses were allowed to continue for 0.25 hours and then quenched by addition of glycine buffer (2.5 mL). The absorbance of the resulting solution was measure at 400 nm. Once this control run of the system gave an absorbance within 0.4–2.0, the potential inhibitors were assayed against this working enzyme solution at final inhibitor and substrate concentrations of 1 and 5 mM, respectively. In the inhibitor assays, deionized water was replaced by the inhibitor (4 mM solution in deionized water). All inhibitors were tested in triplicate, with a control (by substituting the inhibitors with deionized water) and a standard.

C. General Procedure for $K_I$ Determination

Five substrate solutions (usually 2–20M) and five inhibitor solutions (usually 0–200 μM) were prepared. To a -mL test tube were added buffer at the appropriate pH (0.28 mL, phosphate-citrate), working enzyme solution (0.28 mL) and inhibitor solution (0.56 mL). The solution was incubated at 7.C. for 5 minutes. Aliquots (0.1 mL) of this solution were then pipetted into ten separate test tubes. Substrate solution (0.1 mL) was then added to each tube at thirty-second intervals. Duplicate reactions were terminated by addition of glycine buffer (2.5 mL) at the end of 3, 6, 8, 10, and 12 minutes. The amount of released p-nitrophenolate was measured spectrophotometrically at 400 nm. The process was repeated for all combinations of inhibitor and substrate concentrations.

The velocities (V) of substrate hydrolysis at every combination of inhibitor [I] and substrate [S] concentrations were determined by plotting the absorbance values with respect to time and then calculating the slopes of the lines. Double reciprocal plots of 1/V versus 1/[S] at different [I] were then generated. The slopes of each of these lines were then plotted against [I] and the data were fitted to a straight line. The [I]-intercept gave the enzyme-inhibitor dissociation constant. $K_I$ values were also calculated from Hanes-Woolf plots of [S]/V vs. [S] by replotting the [S]/V intercepts versus [I] and ascertaining the [I] intercept. $K_I$ values in the Table represent an average of the two calculations.

EXAMPLE 18

Evaluation of Inhibitory Effects

In accordance with the above General Biological Procedures various of the above prepared amidines, amidrazones, and amidoximes were evaluated to determine their glycosidic enzyme inhibitory capacity.

Figure 1B:
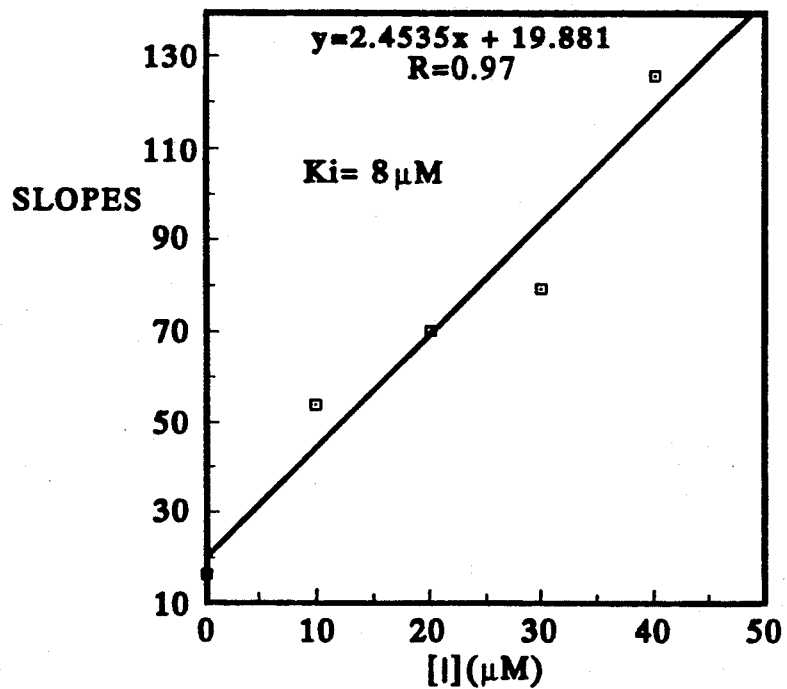
Figure 2A:
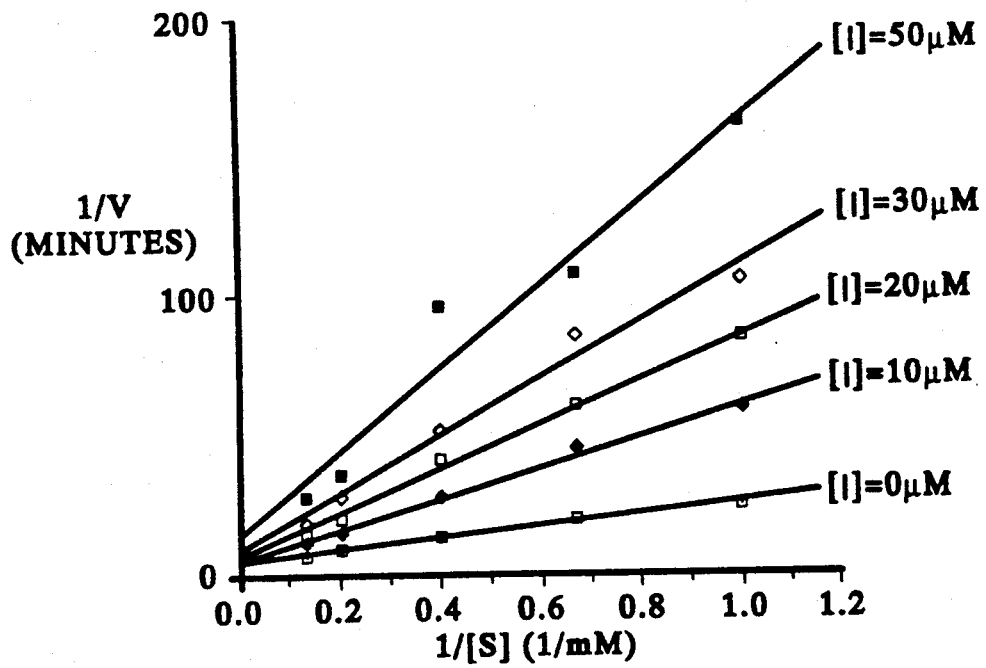
FIGS. 2a and b are the graphs of (a) 1/V vs 1/[S] and (b) L-B slopes vs [I] for the D-glucoamidine of Example 1 against jackbean alpha-mannosidase.
Figure 2B:
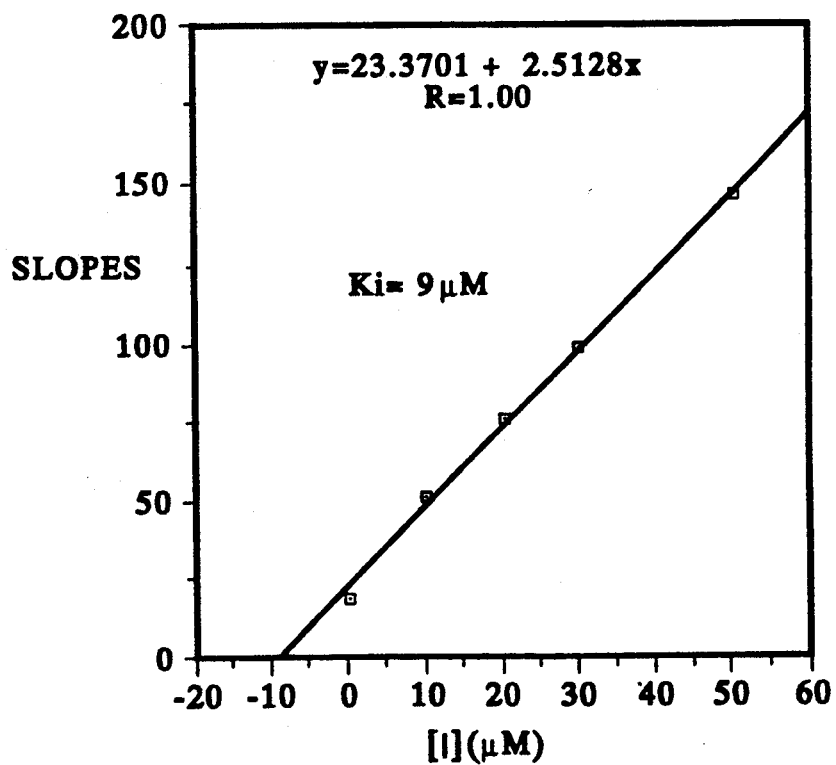
Figure 3A:
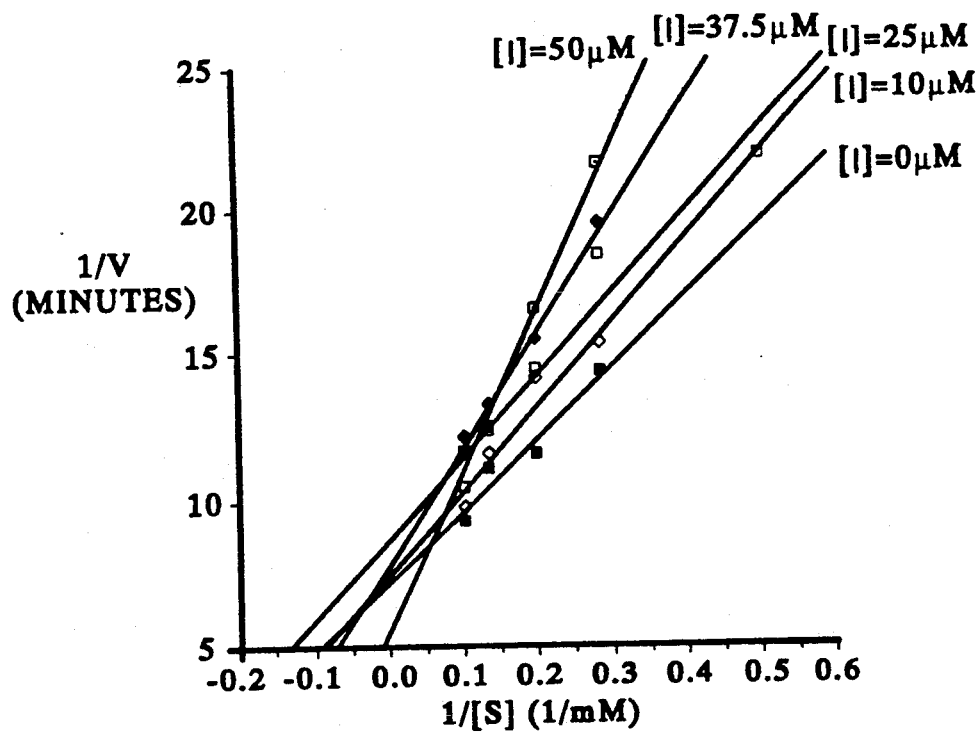
FIGS. 3a and b are the graphs of (a) 1/V vs 1/[S] and (b) L-B slopes vs [I] for the D-glucodimethylamidine of Example 2 against almond β-glucosidase.
Figure 3B:
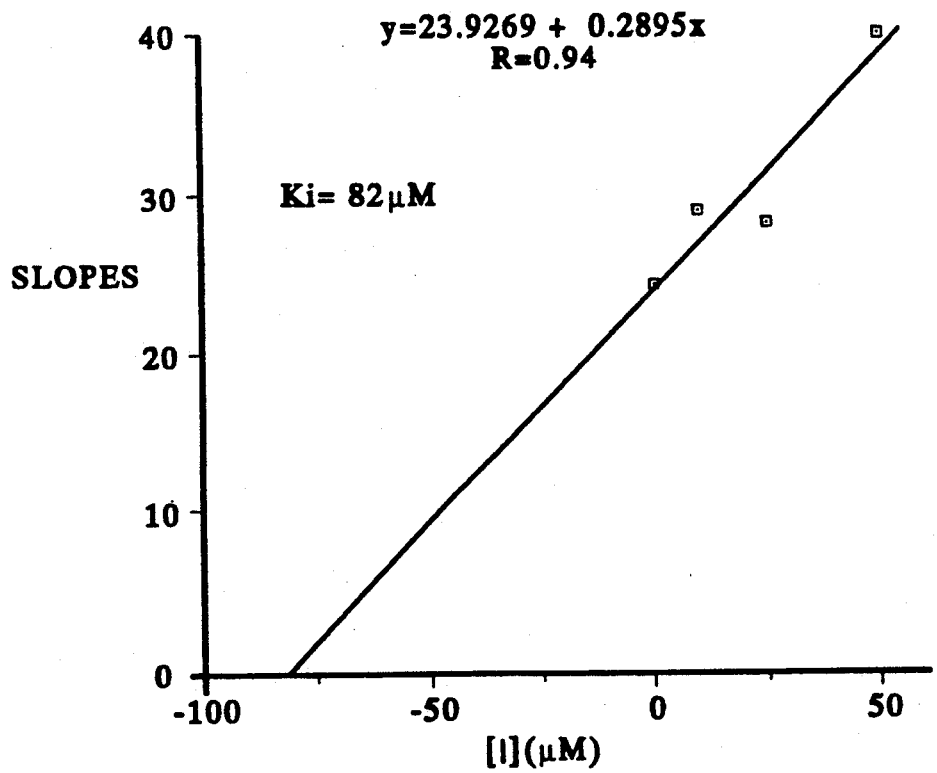
Figure 4A:
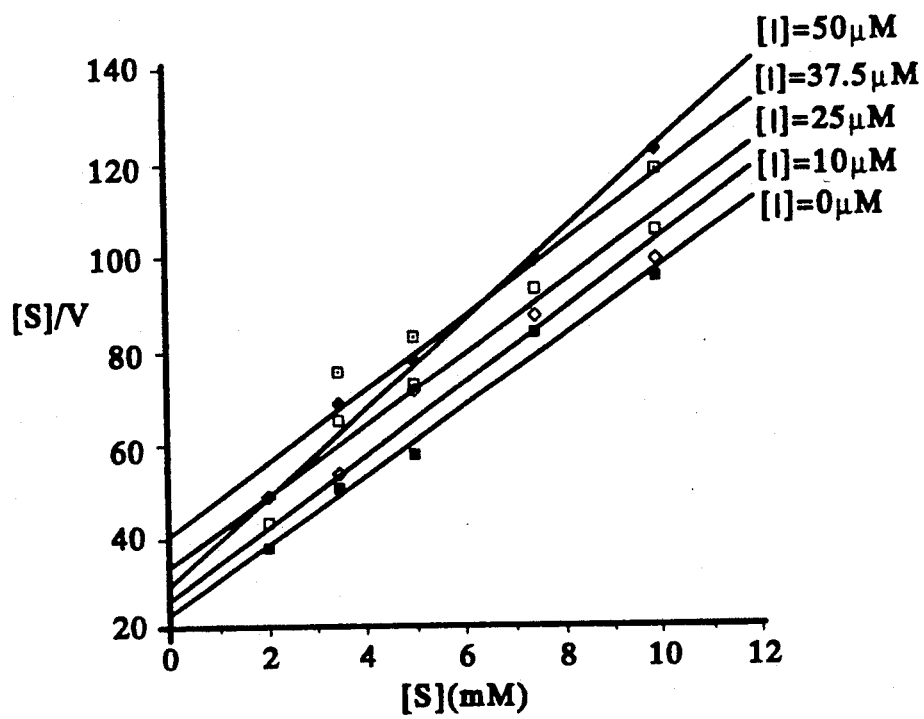
FIGS. 4a and b are the graphs of (a) Hanes-Woolf Plot and (b) Y-intercepts from Hanes-Woolf Treatment plotted vs. [I] for the D-glucodimethylamidine of Example 2 against almond β-glucosidase.
Figure 4B:
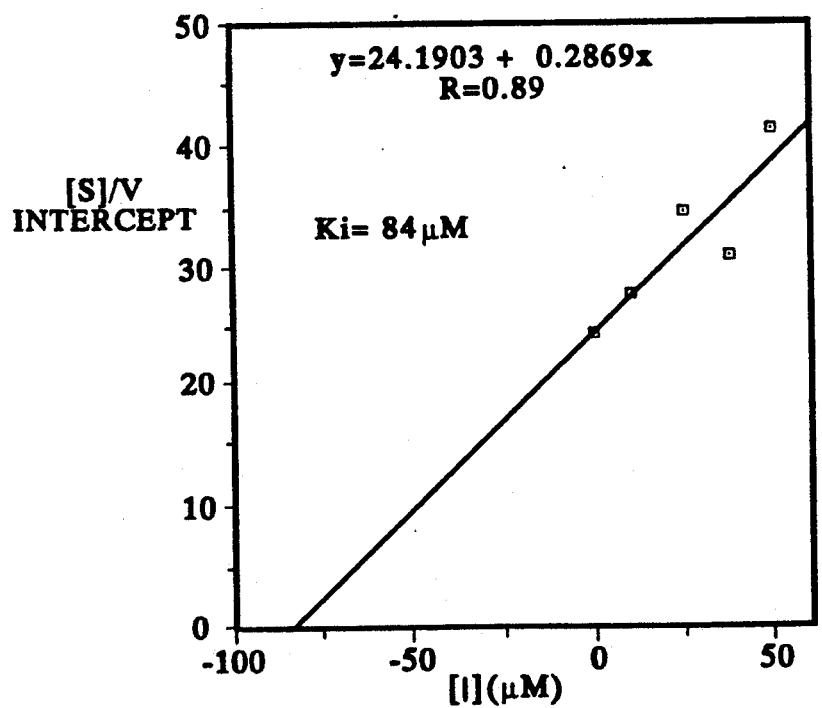
Figure 5A:
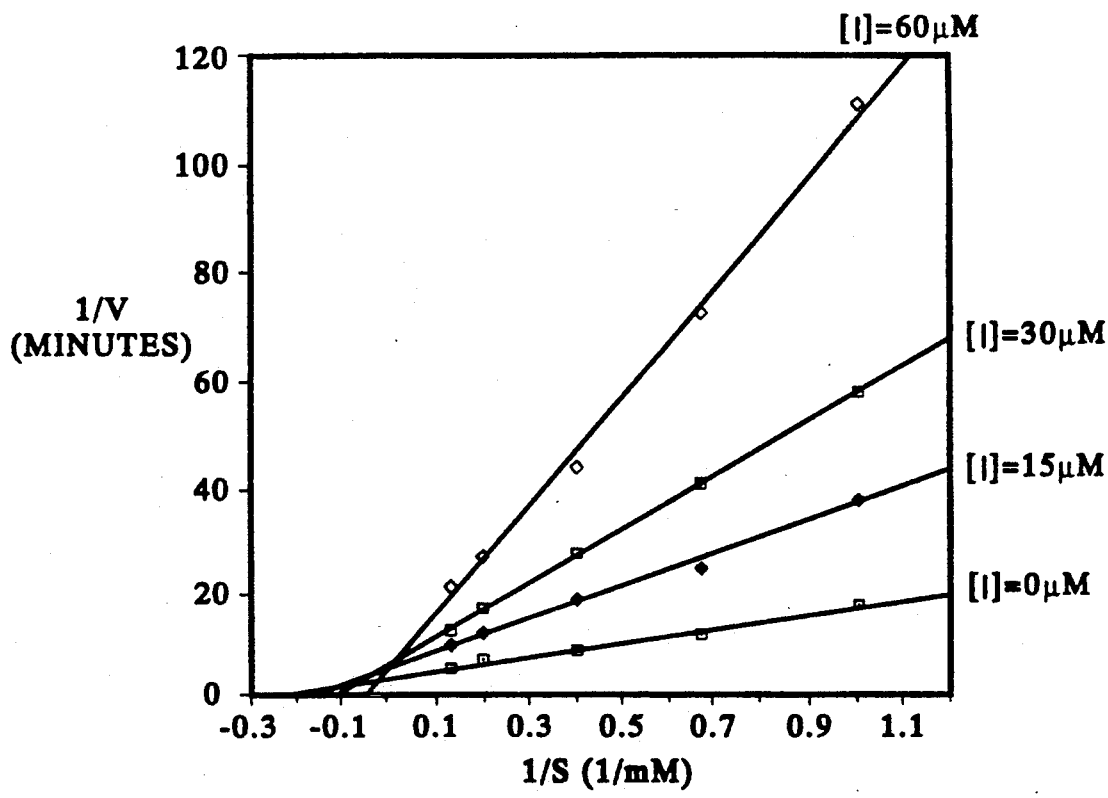
FIGS. 5a and b are the graphs of (a) 1/V vs 1/[S] and (b) L-B slopes vs [I] for the D-glucoamidrazone of Example 8 against almond β-glucosidase.
Figure 5B:
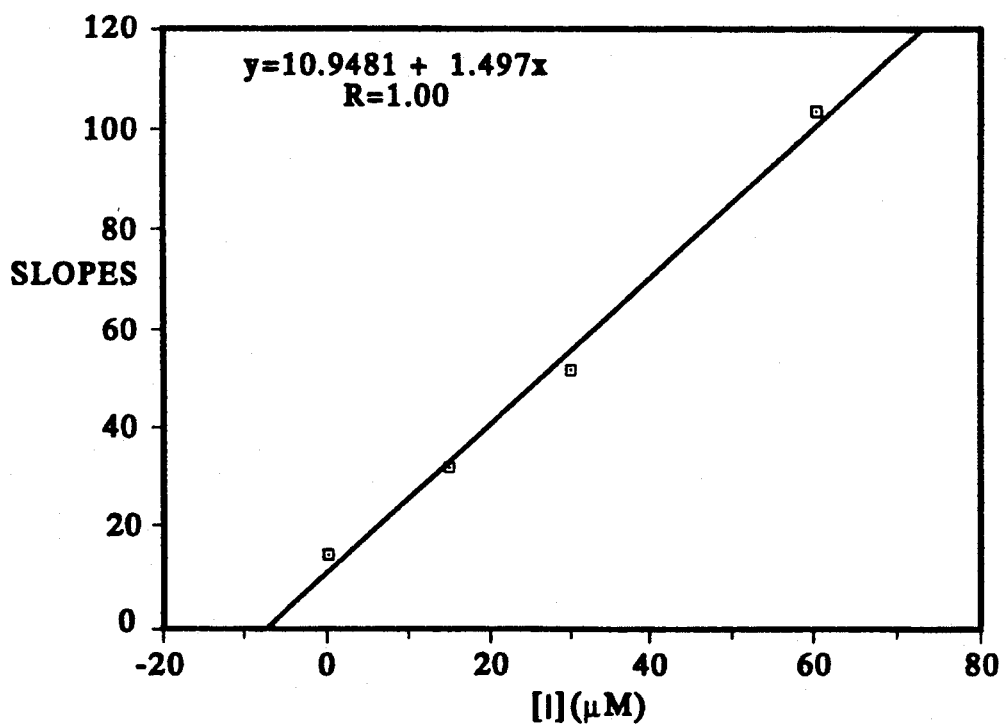
Figure 6A:
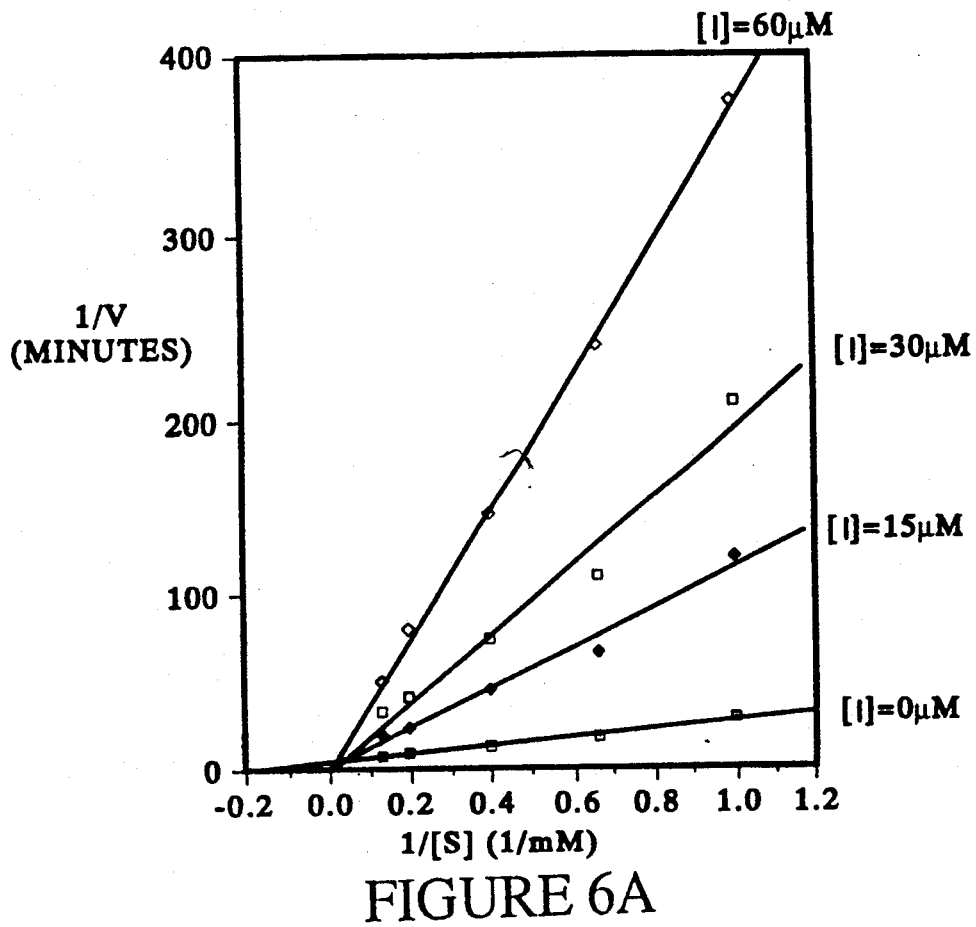
FIGS. 6a and b are the graphs of (a) 1/V vs 1/[S] and (b) L-B slopes vs [I] for the D-glucoamidrazone of Example 8 against jackbean alpha-mannosidase.
Figure 6B:
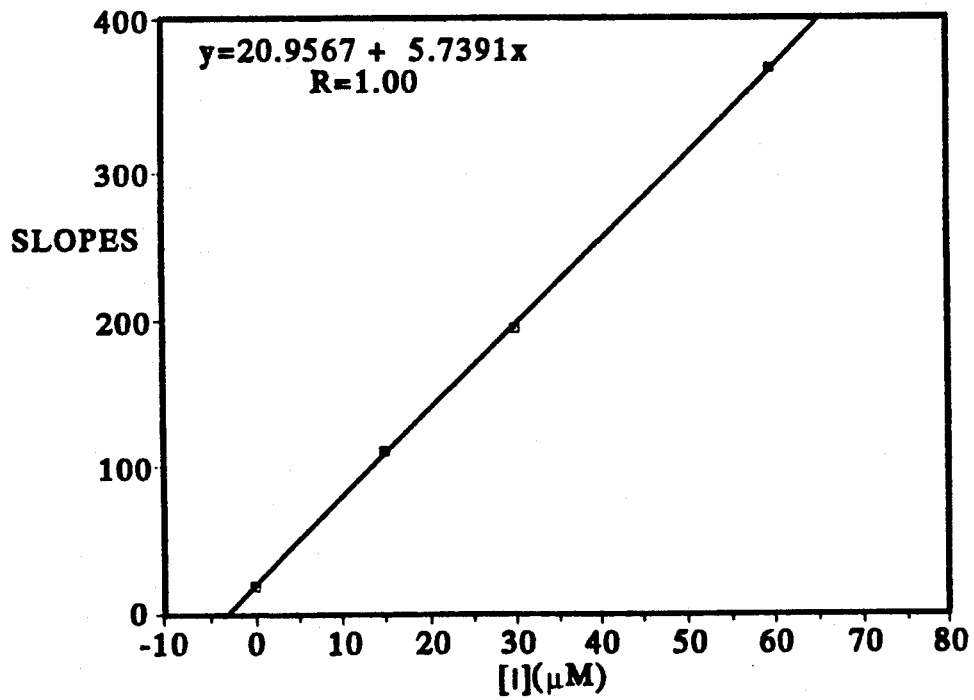
Figure 7A:
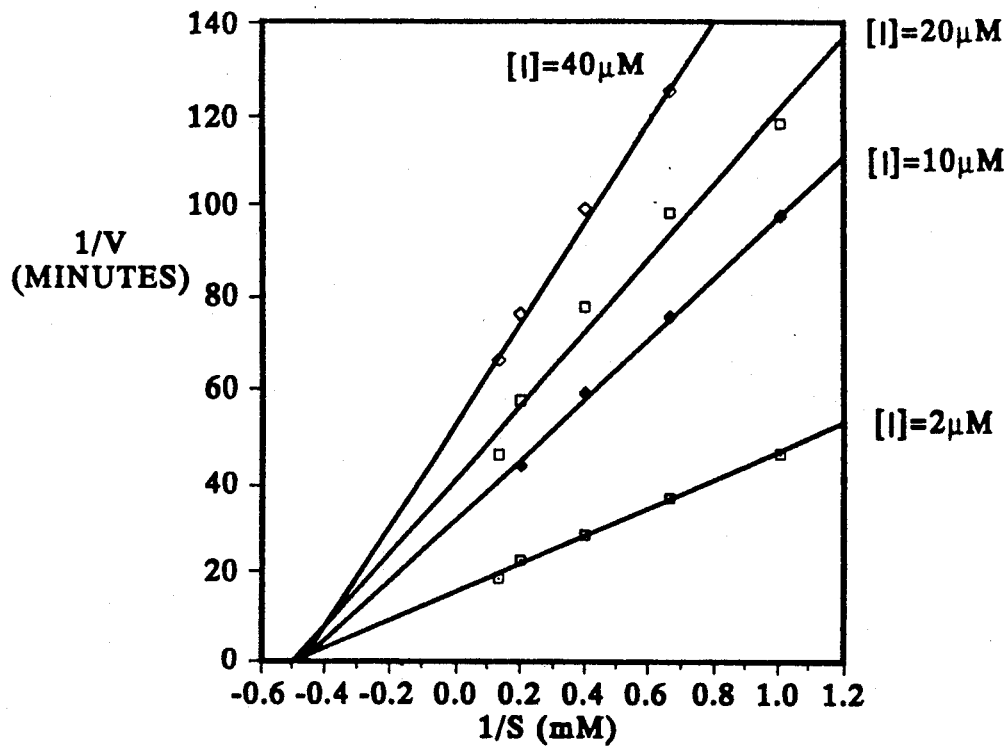
FIGS. 7a and b are the graphs of (a) 1/V vs 1/[S] and (b) L-B slopes vs [I] for the D-glucoamidrazone of Example 8 against bovine β-galactosidase.
Figure 7B:
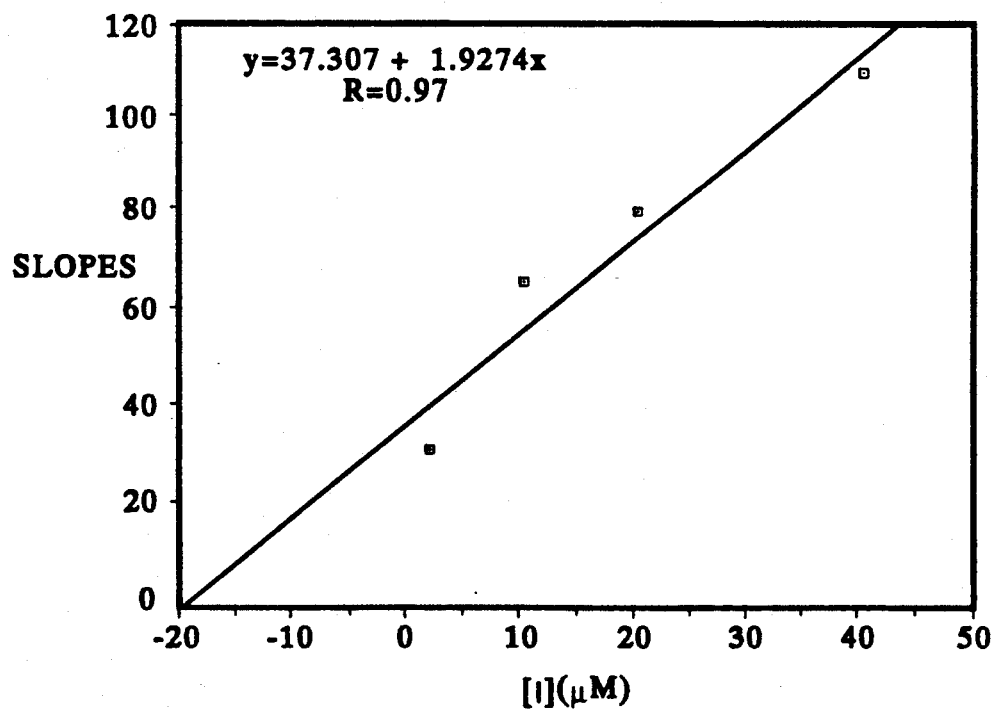
Figure 8A:
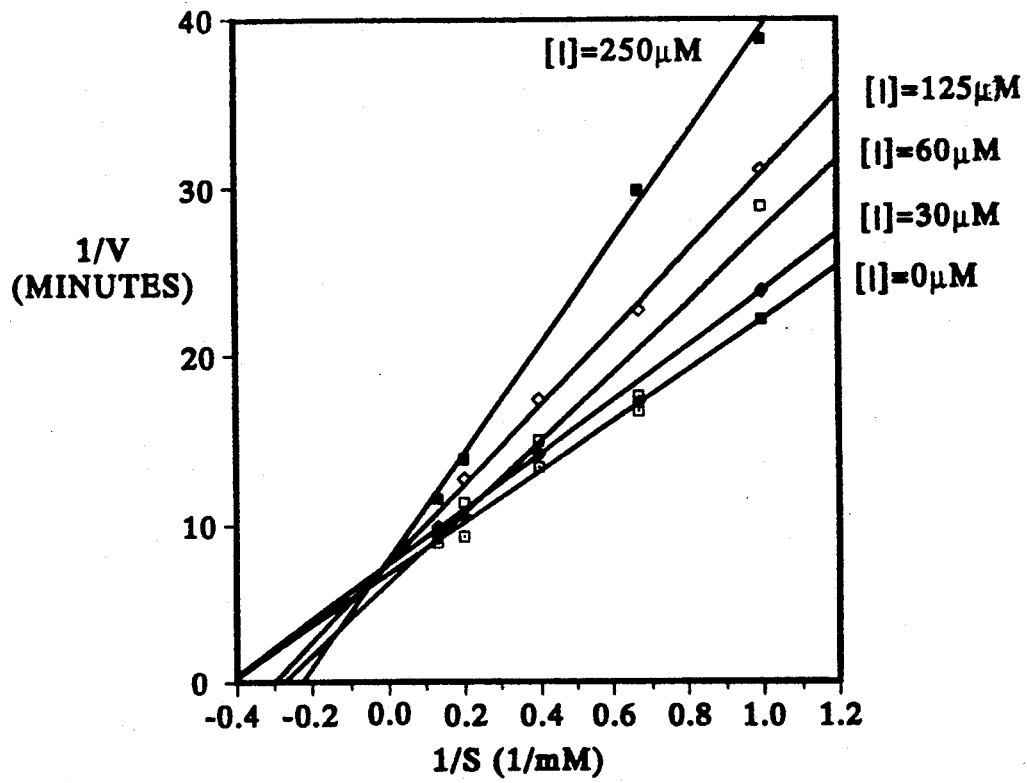
FIGS. 8a and b are the graphs of (a) 1/V vs 1/[S] and (b) L-B slopes vs [I] for the D-mannoamidrazone of Example 9 against almond β-glucosidase.
Figure 8B:
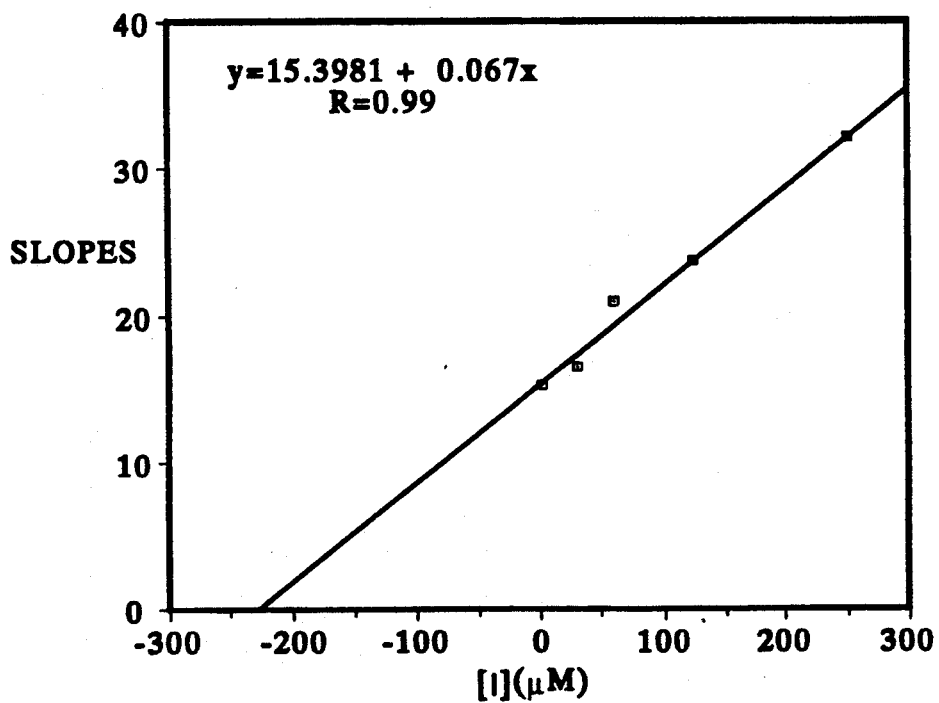
Figure 9A:
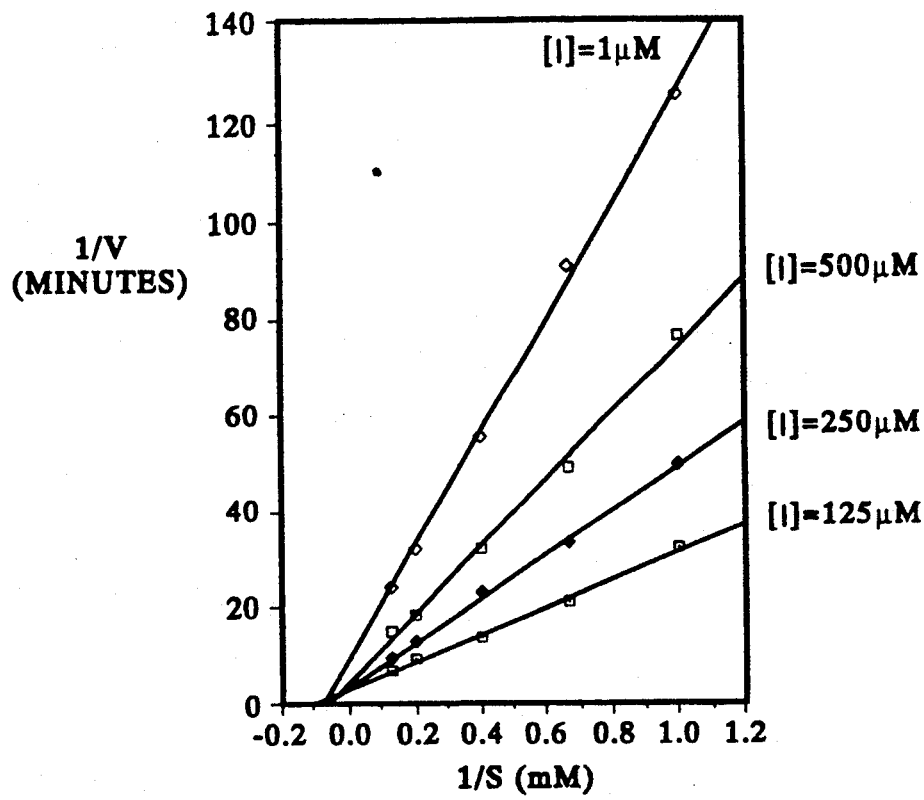
FIGS. 9a and b are the graphs of (a) 1/V vs 1/[S] and (b) L-B slopes vs [I] for the D-mannoamidrazone of Example 9 against jackbean alpha-mannosidase.
Figure 9B:
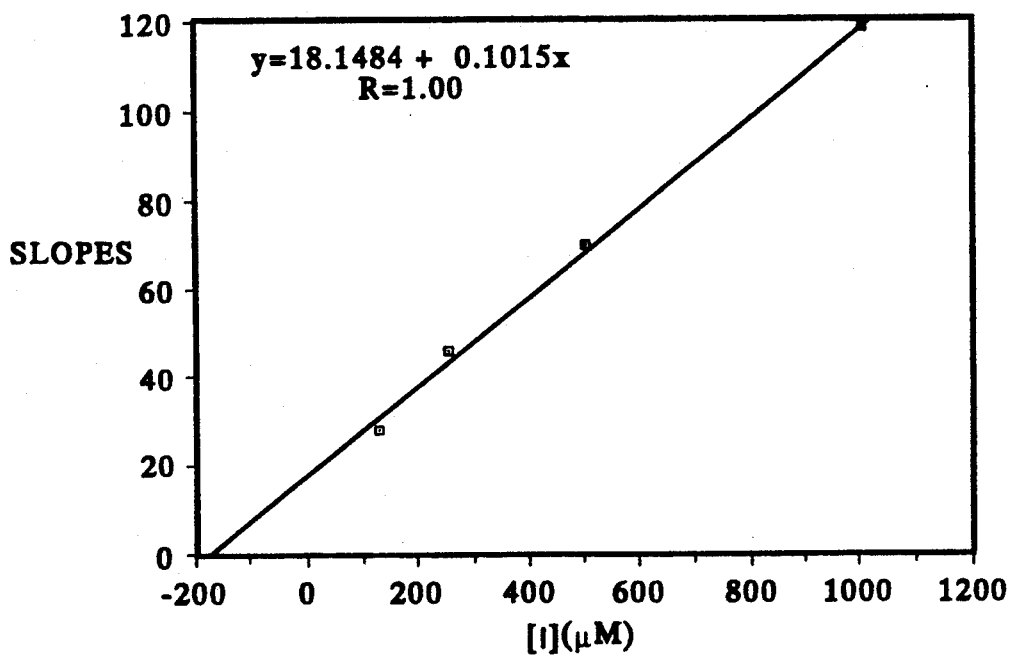
Figure 10A:
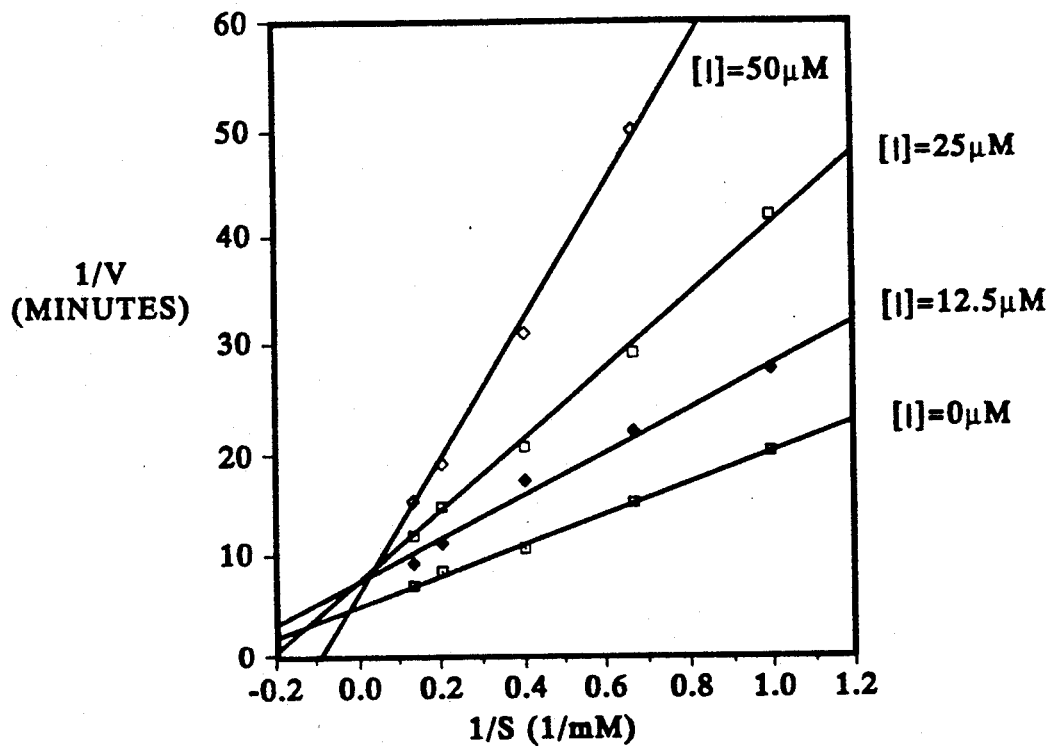
FIGS. 10a and b are the graphs of (a) 1/V vs 1/[S] and (b) L-B slopes vs [I] for the D-glucoamidoxime of Example 12 against almond β-glucosidase.
Figure 10B:
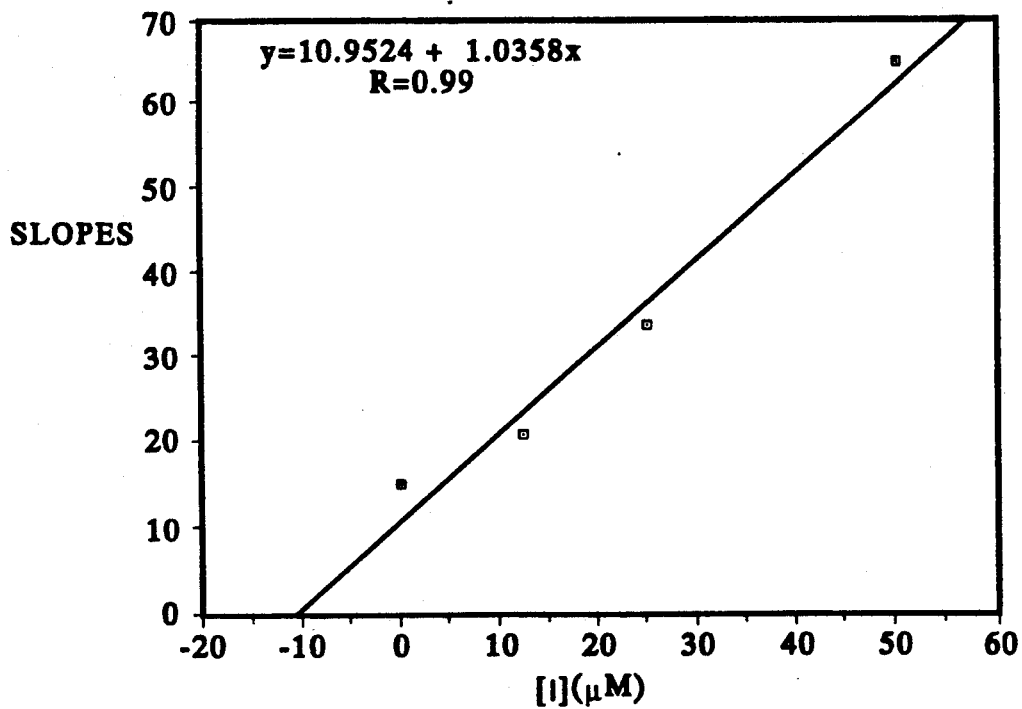
Figure 11A:
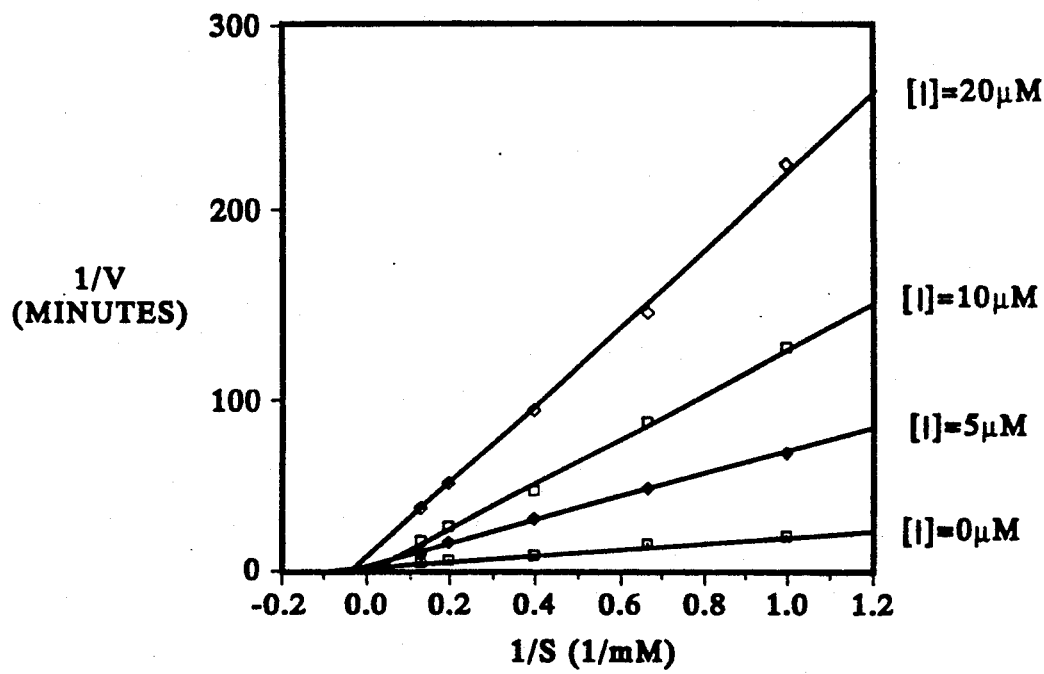
FIGS. 11a and b are the graphs of (a) 1/V vs 1/[S] and (b) L-B slopes vs [I] for the D-mannoamidoxime of Example 14 against jackbean alpha-mannosidase.
Figure 11B:
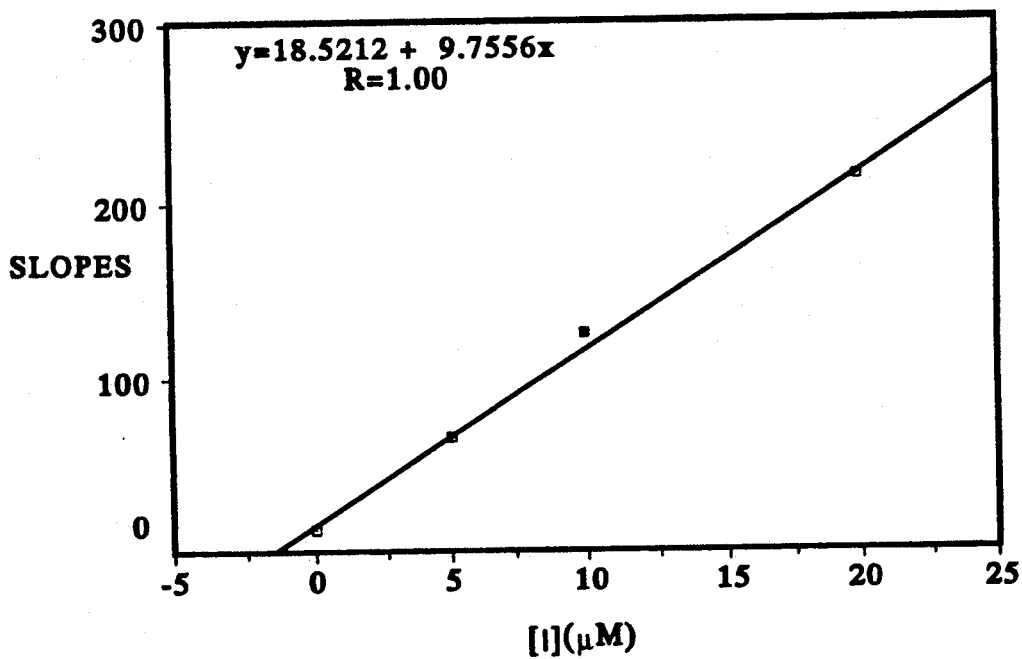

A summary of the results of the assays are provided in Table I below in which the compounds which were tested are identified by the example above by which they were prepared and, in some cases, in graphical form in FIGS. 1–11. In the Table, "potent" means a $K_I$ of less than about 100 μM, "mod" is moderate which means a $K_I$ of from about 100 to 1,000 μM, and "weak" means a $K_I$ of greater than about 1,000 μM.

TABLE I

| Compound | Results of Bioassays in μM | | | | | |
|---|---|---|---|---|---|---|
| | β-Glu pH 5.0 | α-Glu pH 6.6 | amylo-Glu pH 5.0 | α-man pH 5.0 | β-gal pH 7.0 | α-gal pH 6.6 |
| Nojirimycin | 380 | 13 | weak | moderate | weak | mod–none |
| 1 | 8 | none | weak | 9 | potent | none |
| 2 | 83 | none | weak | potent | potent | none |
| 8 | 8.4 ± 0.9 | | | 6.5 ± 3 | 19 | |
| 9 | 205 ± 25 | | | 0.166 ± 0.013 | 57 ± 2.5 | |
| 13 | 13.8 ± 3 | | | 10 ± 2 | | |
| 15 | | | | 2 ± 0.1 | | |

β-glu is almond β-glucosidase
α-glu is yeast α-glucosidase
amylo-glu is *A. niger* amyloglucosidase
α-man is jackbean α-mannosidase
β-gal is bovine β-galactosidase
α-gal is coffee bean α-galactosidase

COMPARATIVE EXAMPLE A

An attempt to prepare D-glucoamidine (Example 1) was made by aminolysis of the corresponding D-glucoiminoether, an alternative synthetic route starting from D-glucolactam as in Example 1. The hydroxyl groups of the lactam were protected by being peracetylated (NaOAc, Ac$_2$O, room temperature, 44 hr) to produce the tetra-O-acetyl lactam which was then treated with Meerwein's salt (Borch, *Tetrahedron Lett.*, 1968, 61–65) (triethyloxonium tetrafluoroborate, CH$_2$Cl$_2$, room temperature, 36 hr) to produce the D-glucoiminoether. Exposure of the iminoether to excess ammonia in methanol regenerated the starting D-glucolactam in 72–84% yield. Attempted aminolysis by treatment with concentrated ammonium hydroxide, anhydrous liquid ammonia, or ammonium chloride also produced the starting lactam as the sole reaction product.

The re-formation of the lactam could be rationalized by postulating initial attack of ammonia on the C-3 acetate to generate an intermediate which could cyclize with loss of ethanol to form an acetamide ketal structure which, upon prolonged exposure to methanolic ammonia would produce the starting lactam. Thus an alternative hydroxyl protecting group, i.e. trimethylsilyl, which would not enter into such neighboring-group participation was tried as described in Example 1. Attempts at preparing the D-glucoiminoether by O-alkylation were unsuccessful. Instantaneous desilylation occurred when the blocked lactam was treated with triethyloxonium tetrafluoroborate, even when buffered with Na$_2$HPO$_4$.

Other literature procedures for O-alkylation of lactams to produce an iminoether (ethyl chloroformate (Suydam et al., *J. Org. Chem.*, 1969, 34, 292–6), dimethylsulfate (Benson, et al., *In Organic Syntheses Collective Volume IV*, Rabjohn, Ed., John Wiley: New York, 1963, pp 588–590), diazomethane (Nishiyama et al., *Tetrahedron Lett.*, 1979, 48, 4671–4)) also failed to produce the corresponding iminoether.

EXAMPLE 19

Alternative Preparation of D-Mannoamidine

The procedure of the first paragraph of Comparative Example A was repeated but starting with the iminoether of D-mannose rather than of D-glucose. Specifically, to a solution of D-mannoiminoether (27 mg, 0.072 mmol, 1.0 equiv) in methanol at −25° C. was added NH$_3$-MeOH solution (4.6M, 3.5 mL). The resulting solution was stirred at −25° C. for 24 hr, at −5° C. for 24 hr, and finally at room temperature for 12 hr. The solution was concentrated in vacuo and chromatographed (7:3:1 CH$_2$Cl$_2$:CH$_3$OH:NH$_4$OH) to afford D-mannoamidine.

Various other examples will be apparent to the person skilled in the art after reading the present disclosure without departing from the spirit and scope of the invention. It is intended that all such other examples be included within the scope of the appended claims.

What is claimed is:

1. The compound D-glucoamidoxime.
2. The compound D-gluco-N-methylamidoxime.
3. The compound D-mannoamidoxime.
4. The compound L-idoamidoxime.

* * * * *